(12) United States Patent
Hess et al.

(10) Patent No.: US 11,638,777 B2
(45) Date of Patent: May 2, 2023

(54) COMPOSITIONS AND METHODS FOR ADHESION TO SURFACES

(71) Applicant: RevBio, Inc., Lowell, MA (US)

(72) Inventors: Brian J. Hess, Charlestown, MA (US); George W. Kay, Sharon, MA (US)

(73) Assignee: RevBio, Inc., Lowell, MA (US)

( * ) Notice: Subject to any disclaimer, the term of this patent is extended or adjusted under 35 U.S.C. 154(b) by 0 days.

(21) Appl. No.: 17/122,816

(22) Filed: Dec. 15, 2020

(65) Prior Publication Data

US 2021/0146004 A1 May 20, 2021

Related U.S. Application Data

(63) Continuation of application No. 15/577,067, filed as application No. PCT/US2016/034830 on May 27, 2016, now abandoned.

(60) Provisional application No. 62/168,630, filed on May 29, 2015.

(51) Int. Cl.

| | | |
|---|---|---|
| *A61L 27/12* | (2006.01) | |
| *A61L 27/02* | (2006.01) | |
| *A61K 6/30* | (2020.01) | |
| *A61K 6/60* | (2020.01) | |
| *A61K 6/75* | (2020.01) | |
| *A61K 6/838* | (2020.01) | |
| *A61K 6/864* | (2020.01) | |
| *A61K 6/876* | (2020.01) | |
| *A61C 5/70* | (2017.01) | |
| *A61C 5/35* | (2017.01) | |
| *A61C 8/00* | (2006.01) | |
| *A61C 13/271* | (2006.01) | |
| *A61F 2/28* | (2006.01) | |
| *A61F 2/44* | (2006.01) | |
| *A61L 24/00* | (2006.01) | |
| *A61L 24/02* | (2006.01) | |
| *A61L 27/36* | (2006.01) | |
| *A61L 27/58* | (2006.01) | |
| *A61F 2/30* | (2006.01) | |

(52) U.S. Cl.
CPC ............... *A61L 27/12* (2013.01); *A61C 5/35* (2017.02); *A61C 5/70* (2017.02); *A61C 8/0009* (2013.01); *A61C 13/26* (2013.01); *A61F 2/2803* (2013.01); *A61F 2/4455* (2013.01); *A61K 6/30* (2020.01); *A61K 6/60* (2020.01); *A61K 6/75* (2020.01); *A61K 6/838* (2020.01); *A61K 6/864* (2020.01); *A61K 6/876* (2020.01); *A61L 24/0005* (2013.01); *A61L 24/0042* (2013.01); *A61L 24/02* (2013.01); *A61L 27/02* (2013.01); *A61L 27/025* (2013.01); *A61L 27/3604* (2013.01); *A61L 27/3616* (2013.01); *A61L 27/58* (2013.01); *A61F 2002/2835* (2013.01); *A61F 2002/30448* (2013.01); *A61L 2400/06* (2013.01); *A61L 2430/02* (2013.01); *A61L 2430/10* (2013.01); *A61L 2430/12* (2013.01); *A61L 2430/24* (2013.01); *A61L 2430/34* (2013.01); *A61L 2430/38* (2013.01)

(58) Field of Classification Search
CPC ........................................................ A61L 27/12
See application file for complete search history.

(56) References Cited

U.S. PATENT DOCUMENTS

| | | |
|---|---|---|
| 5,770,229 A | 6/1998 | Tanihara et al. |
| 2006/0115792 A1 | 6/2006 | Vuillemot |
| 2008/0299093 A1 | 12/2008 | Yang et al. |
| 2010/0121459 A1 | 5/2010 | Garigapati et al. |
| 2011/0277931 A1 | 11/2011 | Garigapati et al. |
| 2012/0129134 A1 | 5/2012 | Walline et al. |
| 2012/0288446 A1 | 11/2012 | Garigapati et al. |
| 2013/0122057 A1 | 5/2013 | Garigapati et al. |
| 2013/0238027 A1 | 9/2013 | Zhang et al. |
| 2015/0050358 A1 | 2/2015 | Seong et al. |

FOREIGN PATENT DOCUMENTS

WO        2007/041587 A2        4/2007

OTHER PUBLICATIONS

International Search Report and Written Opinion dated Oct. 4, 2016 from corresponding International Application No. PCT/US16/34830.

Extended European Search Report in application No. 16804172.1 dated Dec. 20, 2018.

*Primary Examiner* — Michael F Pepitone
(74) *Attorney, Agent, or Firm* — Lando & Anastasi, LLP

(57) ABSTRACT

The present disclosure features adhesive compositions and methods of use thereof related to the medical, veterinary, and dental fields.

18 Claims, 15 Drawing Sheets

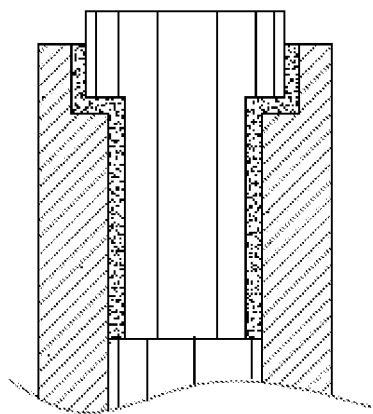
FIG. 22
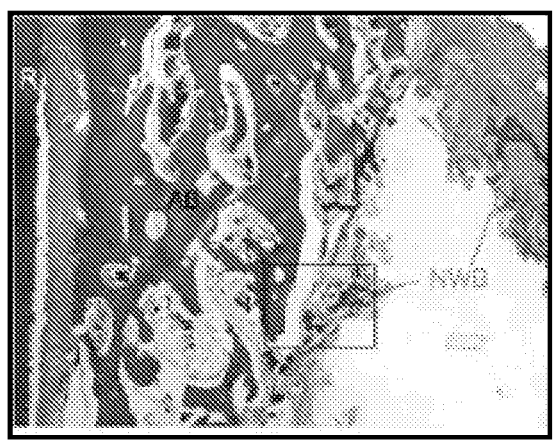 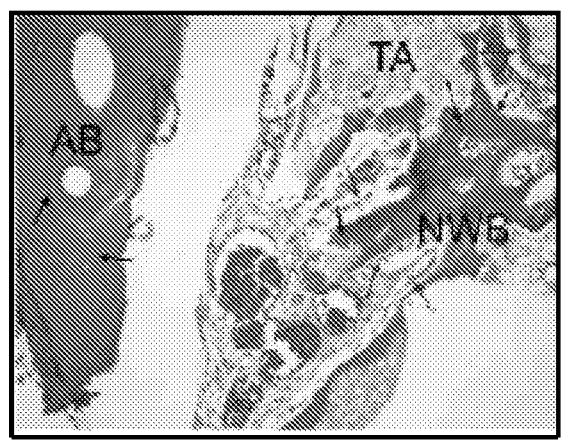
FIG. 23A    FIG. 23B

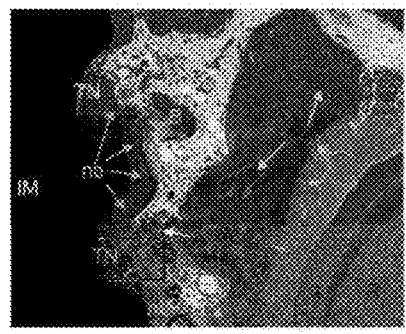 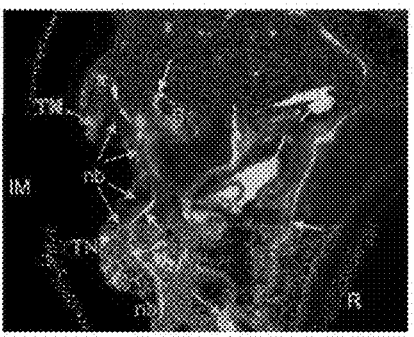
FIG. 27A    FIG. 27B
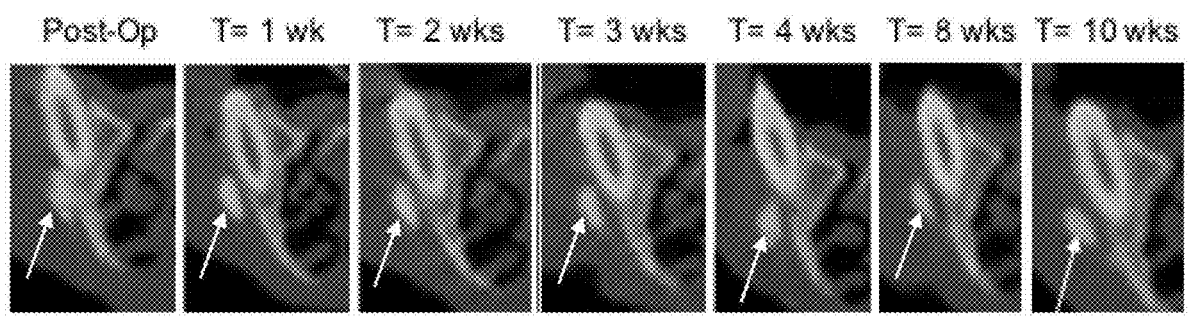
FIG. 28A   FIG. 28B   FIG. 28C   FIG. 28D   FIG. 28E   FIG. 28F   FIG. 28G

  
FIG. 29A    FIG. 29B    FIG. 29C
FIG. 30

COMPOSITIONS AND METHODS FOR ADHESION TO SURFACES

RELATED APPLICATIONS

This application claims priority under 35 U.S.C. § 120 as a continuation of U.S. patent application Ser. No. 15/577,067, titled "COMPOSITIONS AND METHODS FOR ADHESION TO SURFACES," filed Nov. 27, 2017, which is a U.S. National Stage Application under 35 U.S.C. § 371 of International Application No. PCT/US2016/034830, filed May 27, 2016, which claims priority to U.S. Patent Application No. 62/168,630, filed May 29, 2015. The entire contents of each of the foregoing applications are incorporated herein by reference.

FIELD

Embodiments of the disclosure relate to adhesive compositions and methods of use thereof.

BACKGROUND

This application relates generally to adhesive compositions and methods of fixation to structures (e.g., bones, grafts and devices) and methods of forming a barrier or seal. More specifically it applies to medical, veterinary, and dental procedures that aim to attach parts of the bony skeleton to each other or attempt to attach artificial devices to the bony skeleton or calcified tissues of any animal, including a human, or attempt to prevent leaks or communication of fluids through the bony skeleton.

Current practices use a variety of hardware metal fixation devices such as screws, pins, anchors, plates, and rods firmly inserted into drilled holes or reamed cavities to immobilize bony parts, including fracture fragments. These devices might also be artificial devices or prosthetic elements that attach to bone. In the dental market, such a device could be a dental implant anchored into bone with its attached abutment and crown or denture prosthesis. All of these devices utilize their mechanical shape features and frictional forces, and not adhesion, as the means of primary fixation. Alternatively, a bone cement, typically a non-resorbable, organic material structurally related to acrylic acid, is used to lute a prosthesis through engaging surface features, or another device, typically metal, to attach it to bone. Resorbable devices such as screws, pins, anchors, and plates are also used to mechanically attach items such as tendon grafts and bone fragments to the host bone structure.

The above methods rely on the existing volume and density of bone to serve as the medium to house and retain the attachment elements. Because the bone volume and density might be limited by anatomical factors, by trauma, and/or by disease-related processes the means of fixation are often limited and compromised as a result of the lack of favorable volume and strength of the bone substance for fixation. In the long term, the fixation and immobilization further depend on the balance of naturally mediated processes of bone formation and growth, e.g., modeling, remodeling, osteointegration, and resorption to attach bone tissue to the surfaces of the various devices serving this function. The resorbable devices are gradually replaced by bone, which allows the tendon grafts and the host bone to heal together into a mechanically bonded unit.

SUMMARY

In one aspect, the disclosure features a composition possessing the properties of adhesion, conforming to a surface, being capable of luting, and becoming a solid that can be adhesively applied to bone or device surfaces. In some embodiments, the shape of the applied composition can be altered by flowing, molding, forming, or plastic deformation of any other kind, to the desired shape and size prior to it becoming generally rigid and solid.

In some embodiments, the composition may have resorption characteristics such that the body has the ability to replace the material through biological processes with natural bone over time, while substantially maintaining the original volume of the material during application. In some embodiments, this characteristic is termed space or volume maintenance.

In certain embodiments, the formulation of the adhesive composition may vary. It may vary in the ratio of the essential reactants, or it may vary through the addition of materials intended to modify characteristics of the material. The inclusion of these modifiers might modify, but not be limited to, rheological characteristics, setting kinetics, soft tissue interaction, hard tissue interaction, interactions with non-biological materials, interactions with the microflora, adhesive properties, resorption kinetics, proportion of porosity, optical properties, and mechanical properties of the composition. In some embodiments, inclusion of these modifiers might modify the size and number of the internal pores.

In some embodiments, the composition may be applied in layers or volumetric segments in order to build to a desired structure, to fill a void, or to adhere a structure to a surface. These layers or volumetric segments may vary based on the components and the ratio of said components of the composition.

In some embodiments, the composition may be applied in layers or volumetric segments in order to build to a desired structure, to fill a void, or to adhere a structure to a surface. These layers or volumetric segments may vary based on the components and the ratio of said components of the composition. These layers or volumetric segments may be applied at the same time or with various degrees of delay (e.g., between about 5-10 seconds, between about 10-20 seconds, between about 20-60 seconds, between about 1-3 minutes, between about 3-10 minutes, between about 10-30 minutes, between about 0.5 hours-2 hours, between about 2-24 hours, between about 1-7 days, between about 1 week to 1 month, between about 1 month to 1 year, or more than 1 year).

In some embodiments, the interaction of the adhesive composition and the tissues might yield a solid, comprised of bone and the composition applied to it, which has a larger volume than the volume of bone alone prior to the application of the composition. The solid comprised of the bone and the composition adherent to it might also be greater in any dimension.

In some embodiments, the interaction of the adhesive composition and the tissues might yield a solid, comprised of bone and the composition adhesively applied to it. The solid so comprised of bone and the composition might be drilled, milled, reamed, shaved, or otherwise altered in shape.

In some embodiments, the interaction of the adhesive composition and the tissues might yield a solid, comprised of bone and the composition adhesively applied to it. The solid so comprised of bone and the composition might be drilled, milled, reamed, shaved or otherwise altered in shape to accept the attachment of a structure. This attachment may be mediated through, but not limited to, adhesion, cementation, luting, interlocking of shapes, or through frictional forces. The alteration of shape may involve either the bone tissue, or the hardened material, or both components of the solid comprised of both. The attachment of the structure may also be to bone alone, the composition alone, or both. The placement of the structure may be guided by mechanical means to its desired position and orientation in space before the material becomes rigid, thus the structure might be placed with precision and affixed in its desired relationship to the surroundings by the solidification of the material.

In one aspect, the present disclosure features an adhesive composition comprising a multivalent metal compound and a compound of Formula (I) or a salt thereof:

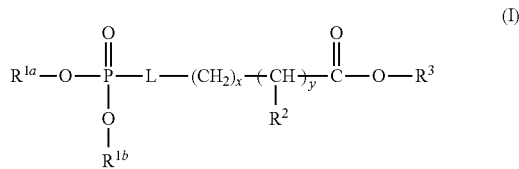

wherein L is O, S, NH, or $CH_2$; each of $R^{1a}$ and $R^{1b}$ is independently H, optionally substituted alkyl, or optionally substituted aryl; $R^2$ is H, $NR^{4a}R^{4b}$, $C(O)R^5$, or $C(O)OR^5$; $R^3$ is H, optionally substituted alkyl, or optionally substituted aryl; each of $R^{4a}$ and $R^{4a}$ is independently H, $C(O)R^6$, or optionally substituted alkyl; $R^5$ is H, optionally substituted alkyl, or optionally substituted aryl; $R^6$ is optionally substituted alkyl or optionally substituted aryl; and each of x and y is independently 0, 1, 2, or 3.

In some embodiments, L is O or S. In some embodiments, L is O. In some embodiments, each of $R^{1a}$ and $R^{1b}$ is independently H. In some embodiments, L is O and each of $R^{1a}$ and $R^{1b}$ is independently H. In some embodiments, $R^2$ is H, $NR^{4a}R^{4b}$ or $C(O)R^5$. In some embodiments, $R^2$ is $NR^{4a}R^{4b}$. In some embodiments, $R^2$ is $NR^{4a}R^{4b}$ and each of $R^{4a}$ and $R^{4b}$ is independently H. In some embodiments, L is O, each of $R^{1a}$ and $R^{1b}$ is H, $R^2$ is $NR^{4a}R^{4b}$, and each of $R^{4a}$ and $R^{4b}$ is independently H. In some embodiments, $R^3$ is H. In some embodiments, L is O, each of $R^{1a}$ and $R^{1b}$ is independently H, $R^2$ is $NR^{4a}R^{4b}$ each of $R^{4a}$ and $R^{4b}$ is independently H, and $R^3$ is H. In some embodiments, each of x and y is 0 or 1. In some embodiments, each of x and y is 1. In some embodiments, L is O, each of $R^{1a}$ and $R^{1b}$ is H, $R^2$ is $NR^{4a}R^{4b}$, each of $R^{4a}$ and $R^{4b}$ is independently H, $R^3$ is H, and each of x and y is 1. In some embodiments, the compound of Formula (I) comprises an organic phosphate compound (e.g., a small organic phosphate compound). In some embodiments, the compound of Formula (I) is phosphoserine.

In another aspect, the disclosure features a method of increasing bone volume, the method comprising: a) preparing an adhesive composition comprising a multivalent metal salt and a compound of Formula (I) (e.g., in an aqueous solution or suspension); and b) applying the composition into an extraction socket; wherein the composition hardens and/or cures in less than about 30 minutes (e.g., less than about 25 minutes, about 20 minutes, about 15 minutes, about 12 minutes, about 10 minutes, about 8 minutes, about 7 minutes, about 6 minutes, about 5 minutes, or less). In some embodiments, the method comprises: a) preparation of an adhesive composition comprising a multivalent metal salt and a small organic phosphate compound in an aqueous solution or suspension; b) adhesive application of the composition into an extraction socket; and c) allowing the composition to remain undisturbed until the composition is hardened, cured, or resorbed and replaced by bone.

In another aspect, the disclosure features a method of filling a bone void resulting from the removal of a bone cyst, granuloma, abscess or similar bone defect, the method comprising: a) preparing an adhesive composition comprising a multivalent metal salt and a compound of Formula (I) (e.g., in an aqueous solution or suspension); and b) applying the composition into said bone void; wherein the composition hardens and/or cures in less than about 30 minutes (e.g., less than about 25 minutes, about 20 minutes, about 15 minutes, about 12 minutes, about 10 minutes, about 8 minutes, about 7 minutes, about 6 minutes, about 5 minutes, or less). In some embodiments, the method comprises: a) preparation of an adhesive composition comprising a multivalent metal salt and a small organic phosphate compound in an aqueous solution or suspension; b) adhesive application of the composition into said bone void; and c) allowing the composition to remain undisturbed until the composition is hardened, cured, or resorbed and replaced by bone. In some embodiments, the bone void results from the loss of natural bone or from the removal of shattered bone fragments.

In another aspect, the present disclosure features a method of increasing bone volume, the method comprising: a) preparing an adhesive composition comprising a multivalent metal salt and a compound of Formula (I) (e.g., in an aqueous solution or suspension); and b) applying the composition onto a substantially flat or convex surface of bone to build volume; wherein the composition hardens and/or cures in less than about 30 minutes (e.g., less than about 25 minutes, about 20 minutes, about 15 minutes, about 12 minutes, about 10 minutes, about 8 minutes, about 7 minutes, about 6 minutes, about 5 minutes, or less). In some embodiments, the method comprises: a) preparation of an adhesive composition comprising a multivalent metal salt and a small organic phosphate compound in an aqueous solution or suspension; b) adhesive application of the composition onto a substantially flat or convex surface of bone to build volume; and c) allowing the composition to remain undisturbed until the composition is hardened, cured, or resorbed and replaced by bone. In some embodiments, the hardening, curing, and/or resorption occurs without the substantial loss of augmented bone volume. The bony surface serving as the site of attachment of the composition might be treated by the removal of the periosteum, by scoring of the surface, by decortications, or might be otherwise altered by mechanical or chemical means, by laser, or by another method. In some embodiments, the other method comprises perforation.

In another aspect, the present disclosure features a method of joining two or more bones, bone fragments, or bone segments adhesively and with capacity to bear load, the method comprising: a) preparing an adhesive composition comprising a multivalent metal salt and a compound of Formula (I) (e.g., in an aqueous solution or suspension); and b) applying the composition onto bony surfaces of adjacent bones, bone fragments, or bone segments to be joined in sufficient amount for the adhesive composition bulk to be continuous; wherein the composition hardens and/or cures in less than about 30 minutes (e.g., less than about 25 minutes, about 20 minutes, about 15 minutes, about 12 minutes, about 10 minutes, about 8 minutes, about 7 minutes, about 6 minutes, about 5 minutes, or less). In some embodiments, the method comprises: a) preparation of an adhesive composition comprising a multivalent metal salt and a small organic phosphate compound in an aqueous solution or suspension; b) adhesive application of the composition onto bony surfaces of adjacent bones, bone fragments, or bone segments to be joined in sufficient amount for the adhesive composition bulk to be continuous; and c) allowing the composition to remain undisturbed until the composition is hardened, cured, or resorbed and replaced by bone. In some embodiments, the allowing the composition to remain undisturbed may be carried out with or without applied compressive forces (e.g., clamps, forceps, fingers) or with or without fixation implants (e.g., membranes, mesh, sutures, k-wires, screws, pins).

In some embodiments, the separation between the bones or bone fragments or bone segments might be caused by a congenital defect (e.g., cleft palate), a trauma (e.g., a jaw or other bone fracture), a disease (e.g., osteosarcoma), may be the result of a resection of bone (e.g., resulting from removal of a neoplasm or necrotic bone), may be the result of surgical treatment (e.g., orthognathic procedure or correction of long bone deformity), or may be a result of loss of small fragments that have lost their mechanical integrity. In some embodiments, the separation between the bones or bone fragments may be caused by an osteochondral fracture or may be the result of a corrective or reconstructive procedure.

In some embodiments, the disclosure features a method of applying the adhesive composition to bone allowing the composition to remain undisturbed until the composition is hardened, cured, or resorbed with or without applied compressive forces (e.g., clamps, forceps, fingers) or with or without fixation implants (e.g., membranes, mesh, sutures, k-wires, screws, pins). In some embodiments, the adhesive composition remains securely attached to bone and does not migrate from its site of application.

In another aspect, the present disclosure features a method of repairing a defect in a bone, the method comprising: a) preparing an adhesive composition comprising a multivalent metal salt and a compound of Formula (I) (e.g., in an aqueous solution or suspension); and b) applying the composition into or onto said bone defect; wherein the composition hardens and/or cures in less than about 30 minutes (e.g., less than about 25 minutes, about 20 minutes, about 15 minutes, about 12 minutes, about 10 minutes, about 8 minutes, about 7 minutes, about 6 minutes, about 5 minutes, or less). In some embodiments, the method comprises: a) preparation of an adhesive composition comprising a multivalent metal salt and a small organic phosphate compound in an aqueous solution or suspension; b) application of the composition adhesively into or onto said bone defect; and c) allowing the composition to remain undisturbed until the composition is hardened, cured, or resorbed and replaced by bone. In certain embodiments, the bone defect is present at the root of a tooth.

In another aspect, the present disclosure features a method of repairing a defect in a tooth, the method comprising: a) preparing an adhesive composition comprising a multivalent metal salt and a compound of Formula (I) (e.g., in an aqueous solution or suspension); and b) applying the composition into or onto said tooth defect; wherein the composition hardens and/or cures in less than about 30 minutes (e.g., less than about 25 minutes, about 20 minutes, about 15 minutes, about 12 minutes, about 10 minutes, about 8 minutes, about 7 minutes, about 6 minutes, about 5 minutes, or less). In some embodiments, the method comprises: a) preparation of an adhesive composition comprising a multivalent metal salt and a small organic phosphate compound in an aqueous solution or suspension; b) adhesive application of the composition into or onto said tooth defect; c) allowing the composition to remain undisturbed until the composition is hardened or cured; and d) finishing the restoration to attain desired shape, contour, and surface characteristics.

In another aspect, the present disclosure features a method of adhesively repairing a defect in a tooth, the method comprising: a) preparing an adhesive composition comprising a multivalent metal salt and a compound of Formula (I) (e.g., in an aqueous solution or suspension); and b) applying the composition into or onto said tooth defect in close proximity or in contact with the dental pulp tissue; wherein the composition hardens and/or cures in less than about 30 minutes (e.g., less than about 25 minutes, about 20 minutes, about 15 minutes, about 12 minutes, about 10 minutes, about 8 minutes, about 7 minutes, about 6 minutes, about 5 minutes, or less). In some embodiments, the disclosure, the method comprising: a) preparation of an adhesive composition comprising a multivalent metal salt and a small organic phosphate compound in an aqueous solution or suspension; b) adhesive application of the composition into or onto said tooth defect in close proximity or in contact with the dental pulp tissue; and c) allowing the composition to remain undisturbed until the composition is hardened or cured.

In another aspect, the present disclosure features a method of attaching a dental device to a tooth, the method comprising: a) preparing an adhesive composition comprising a multivalent metal salt and a compound of Formula (I) (e.g., in an aqueous solution or suspension); and b) applying the composition into or onto a prepared surface of the said tooth or the device to be affixed to the tooth; wherein the composition hardens and/or cures in less than about 30 minutes (e.g., less than about 25 minutes, about 20 minutes, about 15 minutes, about 12 minutes, about 10 minutes, about 8 minutes, about 7 minutes, about 6 minutes, about 5 minutes, or less). In some embodiments, the method comprises: a) preparation of an adhesive composition comprising a multivalent metal salt and a small organic phosphate compound in an aqueous solution or suspension; b) adhesive application of the composition into or onto a prepared surface of the said tooth or the device to be adhesively affixed to the tooth; c) orienting the device in the desired special relationship with the tooth; and d) allowing the composition to remain undisturbed until the composition is hardened or cured. The dental device might be a post, a dental crown restoration, a fixed partial denture, or a similar device.

In another aspect, the present disclosure features a method of adhesively attaching a device (e.g., prosthetic abutment, implant crown restoration, fixed partial denture, or prosthetic limb) to a retaining device (e.g., endosseous implant, dental implant, or amputation stump implant), the method comprising: a) preparing an adhesive composition comprising a multivalent metal salt and a compound of Formula (I) (e.g., in an aqueous solution or suspension); and b) applying the composition into or onto a prepared surface of the said retaining device or the device to be affixed to the retaining device; wherein the composition hardens and/or cures in less than about 30 minutes (e.g., less than about 25 minutes, about 20 minutes, about 15 minutes, about 12 minutes, about 10 minutes, about 8 minutes, about 7 minutes, about 6 minutes, about 5 minutes, or less). In some embodiments, the method comprises: a) preparation of an adhesive composition comprising a multivalent metal salt and a small organic phosphate compound in an aqueous solution or suspension; b) adhesive application of the composition into or onto a prepared surface of the said retaining device or the device to be adhesively affixed to the retaining device; c) orienting the device in the desired special relationship with the retaining device; and d) allowing the composition to remain undisturbed until the composition is hardened or cured. The device might be a post, a dental crown restoration, a fixed partial denture, a prosthetic limb element, or a similar device.

In another aspect, the present disclosure features a method of adhesively sealing the gap between a device (e.g., prosthetic abutment, implant crown restoration, fixed partial denture, prosthetic limb) and a retaining device (e.g., endosseous implant, dental implant, amputation stump implant), the method comprising: a) preparing an adhesive composition comprising a multivalent metal salt and a compound of Formula (I) (e.g., in an aqueous solution or suspension); and b) applying the composition into or onto a prepared surface of the said retaining device or the device to be adhesively affixed to the retaining device; wherein the composition hardens and/or cures in less than about 30 minutes (e.g., less than about 25 minutes, about 20 minutes, about 15 minutes, about 12 minutes, about 10 minutes, about 8 minutes, about 7 minutes, about 6 minutes, about 5 minutes, or less). In some embodiments, the method comprises: a) preparation of an adhesive composition comprising a multivalent metal salt and a small organic phosphate compound in an aqueous solution or suspension; b) adhesive application of the composition into or onto a prepared surface of the said retaining device or the device to be adhesively affixed to the retaining device; c) orienting the device in the desired special relationship with the retaining device; and d) allowing the composition to remain undisturbed until the composition is hardened or cured. The device might be a post, a dental crown restoration, a fixed partial denture, a prosthetic limb element, or a similar device.

In any embodiment, the method may further comprise the placement of a structure (e.g., an implant, graft, or device) into the composition prior to hardening or curing of said composition or prior to the resorption and replacement of the composition by bone, e.g., as described in step c). In any embodiment, the method may further comprise the placement of a structure (e.g., an implant, graft, or device) into the composition after the application of the composition as described in step b) (e.g., about 5 seconds, about 10 seconds, about 30 seconds, about 60 seconds, about 2 minutes, about 5 minutes, about 10 minutes, or longer) but prior to the hardening or curing of said composition, or prior to the resorption and replacement of the composition by bone (e.g., as described in step c).

In some embodiments, the disclosure features a method of installing a bone implant or device, the method comprising: a) preparing an adhesive composition comprising a multivalent metal salt and a compound of Formula (I) (e.g., a small organic phosphate compound) in an aqueous solution or suspension; b) applying the composition into an extraction socket in a bone and or the surface of the implant or device; and c) installing said implant or device into the composition; wherein the composition hardens and/or cures in less than about 30 minutes (e.g., less than about 25 minutes, about 20 minutes, about 15 minutes, about 12 minutes, about 10 minutes, about 8 minutes, about 7 minutes, about 6 minutes, about 5 minutes, or less).

In some embodiments, the disclosure features a method of installing a bone implant or device, the method comprising: a) preparing an adhesive composition comprising a multivalent metal salt and a compound of Formula (I) (e.g., a small organic phosphate compound) in an aqueous solution or suspension; b) placing said implant or device into an extraction socket in a bone; and c) applying the composition to the installation site, e.g., to secure the implant or device to the bone; wherein the composition hardens and/or cures in less than about 30 minutes (e.g., less than about 25 minutes, about 20 minutes, about 15 minutes, about 12 minutes, about 10 minutes, about 8 minutes, about 7 minutes, about 6 minutes, about 5 minutes, or less).

In some embodiments, the disclosure features a method of closing a wound, the method comprising: a) preparing an adhesive composition comprising a multivalent metal salt and a compound of Formula (I) (e.g., a small organic phosphate compound) in an aqueous solution or suspension; and b) injecting the composition into, on top of, or adjacent to a wound site; wherein the composition hardens and/or cures in less than about 30 minutes (e.g., less than about 25 minutes, about 20 minutes, about 15 minutes, about 12 minutes, about 10 minutes, about 8 minutes, about 7 minutes, about 6 minutes, about 5 minutes, or less). In some embodiments, the method prevents the movement of microbes (e.g., bacteria, fungi, viruses, or combinations thereof) into the interior of the wound.

In some embodiments, the disclosure features a method of sealing a site or fistula from the incursion or communication of fluids (e.g., cerebral spinal fluid or blood) or materials, the method comprising: a) preparing an adhesive composition comprising a multivalent metal salt and a compound of Formula (I) (e.g., a small organic phosphate compound) in an aqueous solution or suspension; and b) injecting the composition into, on top of, or adjacent to the site; wherein the composition hardens and/or cures in less than about 30 minutes (e.g., less than about 25 minutes, about 20 minutes, about 15 minutes, about 12 minutes, about 10 minutes, about 8 minutes, about 7 minutes, about 6 minutes, about 5 minutes, or less). In some embodiments, the fluids or materials comprise microbes (e.g., bacteria, fungi, viruses, or combinations thereof).

In some embodiments, the disclosure features a method of controlling excessive bleeding from a wound which involves injury to bone or a fracture of a bone, the method comprising: a) preparing an adhesive composition comprising a multivalent metal salt and a compound of Formula (I) (e.g., a small organic phosphate compound) in an aqueous solution or suspension; b) applying or injecting the composition into, on top of, or adjacent to the bone injury site; and c) re-approximating the bony fragments to reduce the gap between the bony fragments as to occlude the blood flow from the site of the injury to the bone; wherein the composition hardens and/or cures in less than about 30 minutes (e.g., less than about 25 minutes, about 20 minutes, about 15 minutes, about 12 minutes, about 10 minutes, about 8 minutes, about 7 minutes, about 6 minutes, about 5 minutes, or less). In some embodiments, such application of the adhesive composition might be made in an urgent setting such as a battlefield, a site of trauma, an ambulance, a medevac helicopter, or at a trauma center. In some embodiments, such applications may be made as part of a routine surgical procedure. In some embodiments, such application of the composition may be made as a temporary dressing. In some embodiments, such application of the composition may be made as a definite treatment.

In some embodiments, the disclosure features a method of controlling excessive bleeding from a wound which involves injury of a bone or a fracture of a bone, the method comprising: a) preparing an adhesive composition comprising a multivalent metal salt and a compound of Formula (I) (e.g., a small organic phosphate compound) in an aqueous solution or suspension; b) applying or injecting the composition into, on top of, or adjacent to the bone injury site; and c) applying a solid material to the composition applied on the bone to occlude the blood flow from the injured surface of the bone; wherein the composition hardens and/or cures in less than about 30 minutes (e.g., less than about 25 minutes, about 20 minutes, about 15 minutes, about 12 minutes, about 10 minutes, about 8 minutes, about 7 minutes, about 6 minutes, about 5 minutes, or less). In some embodiments, such solid material might be comprised of resorbable material (e.g., collagen or polyglycolic acid) or non-resorbable material (e.g., titanium). In some embodiments, such solid material may be in the form of a plate, a plug, or a soft pliable material (e.g., woven or non-woven fabric or a mesh). In some embodiments, such application of the composition might be made in an urgent setting such as a battlefield, a site of trauma, or at a trauma center. In some embodiments, such applications may be made as part of a routine surgical procedure. In some embodiments, such application of the composition may be made as a temporary dressing. In some embodiments, such application of the composition may be made as a definite treatment.

In some embodiments, the disclosure features a method of controlling excessive bleeding from a wound which involves injury of a bone or a fracture of a bone the method comprising: a) preparing an adhesive composition comprising a multivalent metal salt and a compound of Formula (I) (e.g., a small organic phosphate compound) in an aqueous solution or suspension; b) applying the composition onto a solid material; and c) applying the solid material carrying the applied composition applied to the injured bone to occlude the blood flow from the injured surface of the bone; wherein the composition hardens and/or cures in less than about 30 minutes (e.g., less than about 25 minutes, about 20 minutes, about 15 minutes, about 12 minutes, about 10 minutes, about 8 minutes, about 7 minutes, about 6 minutes, about 5 minutes, or less). In some embodiments, such solid material might be comprised of resorbable material (e.g., collagen or polyglycolic acid) or non-resorbable material (e.g., titanium). In some embodiments, such solid material may be in the form of a plate, a plug, or a soft pliable material (e.g., woven or non-woven fabric or a mesh). In some embodiments, such application of the composition might be made in an urgent setting such as a battlefield, a site of trauma, or at a trauma center. In some embodiments, such applications may be made as part of a routine surgical procedure. In some embodiments, such application of the composition may be made as a temporary dressing. In some embodiments, such application of the composition may be made as a definite treatment.

In some embodiments, the disclosure features a method of controlling excessive bleeding from a wound which involves injury to an artery near or about the foramen marking its emergence from within the body of the bone, the method comprising: a) preparing an adhesive composition comprising a multivalent metal salt and a compound of Formula (I) (e.g., a small organic phosphate compound) in an aqueous solution or suspension; b) injecting the composition into or on top of the foramen through which the artery normally emerges from the bone or to the exits the or adjacent to the bone injury site; and c) occluding the blood flow by pressure application; wherein the composition hardens and/or cures in less than about 30 minutes (e.g., less than about 25 minutes, about 20 minutes, about 15 minutes, about 12 minutes, about 10 minutes, about 8 minutes, about 7 minutes, about 6 minutes, about 5 minutes, or less). In some embodiments, such application of the composition might be made in an urgent setting such as a battlefield, a site of trauma, or at a trauma center. In some embodiments, such applications may be made as part of a routine surgical procedure. In some embodiments, such application of the composition may be made as a temporary dressing. In some embodiments, such application of the composition may be made as a definite treatment.

In some embodiments, the disclosure features a method of controlling excessive bleeding from a wound which involves injury to an artery through trans-section, rupture or other separation of the bone as the artery courses through its canal in the bone, the method comprising: a) preparing an adhesive composition comprising a multivalent metal salt and a compound of Formula (I) (e.g., a small organic phosphate compound) in an aqueous solution or suspension; b) injecting the composition into or on top of the opening into the canal through which the artery normally courses but from which the hemorrhage is now flowing; and c) occluding the blood flow by pressure application (e.g., either directly or through the use of the composition being applied under hydrostatic pressure through a device such as a cannula or a specialized syringe tip); wherein the composition hardens and/or cures in less than about 30 minutes (e.g., less than about 25 minutes, about 20 minutes, about 15 minutes, about 12 minutes, about 10 minutes, about 8 minutes, about 7 minutes, about 6 minutes, about 5 minutes, or less). In some embodiments, such application of the composition might be made in an urgent setting such as a battlefield, a site of trauma, or at a trauma center. In some embodiments, such applications may be made as part of a routine surgical procedure. In some embodiments, such application of the composition may be made as a temporary dressing. In some embodiments, such application of the composition may be made as a definite treatment.

In some embodiments, the disclosure features a method of restoring a bone deformity to a primary palate, the method comprising: a) preparing an adhesive composition comprising a multivalent metal salt and a compound of Formula (I) (e.g., a small organic phosphate compound) in an aqueous solution or suspension; and b) applying the composition into, on top of, or adjacent to the bone deformity or the bone deficiency; wherein the composition hardens and/or cures in less than about 30 minutes (e.g., less than about 25 minutes, about 20 minutes, about 15 minutes, about 12 minutes, about 10 minutes, about 8 minutes, about 7 minutes, about 6 minutes, about 5 minutes, or less).

In some embodiments, the disclosure features a method of restoring load bearing capacity to bones sectioned into segments as a part of an orthognathic procedure (e.g., fixation of the condylar segment to the body of the mandible after a sagittal split osteotomy, oblique osteotomy, a LaForte osteotomy, or a genioplasty procedure), the method comprising: a) preparing an adhesive composition comprising a multivalent metal salt and a compound of Formula (I) (e.g., a small organic phosphate compound) in an aqueous solution or suspension; b) applying the composition into, on top of, or adjacent to the bone surface; and c) placement of the bone fragments into desirable special relationship; wherein the composition hardens and/or cures in less than about 30 minutes (e.g., less than about 25 minutes, about 20 minutes, about 15 minutes, about 12 minutes, about 10 minutes, about 8 minutes, about 7 minutes, about 6 minutes, about 5 minutes, or less). The application of the composition might occur once or more than once. The reapplication of the composition might occur during steps b), c), or during the hardening and/or curing of the composition as described above.

In some embodiments, the disclosure features a method of additively reshaping, molding or contouring the outer surface of a bone (e.g., in the facial region, forehead, mandible, or any articulating surface of bone), the method comprising: a) preparing an adhesive composition comprising a multivalent metal salt and a compound of Formula (I) (e.g., a small organic phosphate compound) in an aqueous solution or suspension; and b) applying the composition to the desired region of the bone; wherein the composition hardens and/or cures in less than about 30 minutes (e.g., less than about 25 minutes, about 20 minutes, about 15 minutes, about 12 minutes, about 10 minutes, about 8 minutes, about 7 minutes, about 6 minutes, about 5 minutes, or less). In some embodiments, the mass of the composition might be modified in size or shape prior to its hardening. In some embodiments, the mass of the composition might be modified in size or shape following its hardening. In some embodiments, the procedure might be performed in conjunction with other bone contouring processes that are subtractive.

In some embodiments, the disclosure features a method of additively reshaping, molding, or contouring the outer surface of a bone in the facial region of a subject undergoing a cosmetic treatment, the method comprising: a) preparing an adhesive composition comprising a multivalent metal salt and a compound of Formula (I) (e.g., a small organic phosphate compound) in an aqueous solution or suspension; and b) applying the composition adhesively to the desired region; wherein the composition hardens and/or cures in less than about 30 minutes (e.g., less than about 25 minutes, about 20 minutes, about 15 minutes, about 12 minutes, about 10 minutes, about 8 minutes, about 7 minutes, about 6 minutes, about 5 minutes, or less). In some embodiments, the facial region comprises the nose, chin, cheek, mid-face, or forehead.

In some embodiments, the disclosure features a method of treating a subject suffering from a disease or condition, the method comprising: a) preparing an adhesive composition comprising a multivalent metal salt and a compound of Formula (I) (e.g., a small organic phosphate compound) in an aqueous solution or suspension; and b) applying the composition to the desired region; wherein the composition hardens and/or cures in less than about 30 minutes (e.g., less than about 25 minutes, about 20 minutes, about 15 minutes, about 12 minutes, about 10 minutes, about 8 minutes, about 7 minutes, about 6 minutes, about 5 minutes, or less). In some embodiments, the disease or condition comprises cancer (e.g., osteosarcoma), osteoporosis, rickets, osteogenesis imperfecta, fibrous dysplasia, Paget's disease of the bone, hearing loss, renal osteodystrophy, a malignancy of the bone, infection of the bone, osteonecrosis, or other genetic or developmental disease. In some embodiments, the disease or disorder comprises fibrous dysplasia or nerve compression. In some embodiments, the subject has decay, fracture, attrition, erosion, abrasion, or abfraction of a bone, or another cause of bone substance loss. In some embodiments, the bone comprises a tooth. In some embodiments, the subject is suffering from or has been diagnosed with tooth decay, fracture, attrition, erosion, abrasion, abfraction, or another cause of tooth substance loss. In some embodiments, the calcified tissue loss is the result of cutting of said tissues during a surgical or dental procedure.

In some embodiments, the disclosure features a method of repairing a bone or other calcified tissue defect in a subject suffering from a disease or condition, the method comprising: a) preparing an adhesive composition comprising a multivalent metal salt and a compound of Formula (I) (e.g., a small organic phosphate compound) in an aqueous solution or suspension; and b) applying the composition to the desired region; wherein the composition hardens and/or cures in less than about 30 minutes (e.g., less than about 25 minutes, about 20 minutes, about 15 minutes, about 12 minutes, about 10 minutes, about 8 minutes, about 7 minutes, about 6 minutes, about 5 minutes, or less). In some embodiments, the disease or condition comprises cancer (e.g., osteosarcoma), osteoporosis, rickets, osteogenesis imperfecta, fibrous dysplasia, Paget's disease of the bone, hearing loss, renal osteodystrophy, a malignancy of the bone, infection of the bone, osteonecrosis, or other genetic or developmental disease. In some embodiments, the subject is suffering from or has been diagnosed with tooth decay, fracture, attrition, erosion, abrasion, abfraction, or another cause of tooth substance loss. In some embodiments, the calcified tissue loss is the result of cutting of said tissues during a surgical or dental procedure.

In some embodiments, the disclosure features a method of strengthening a bone in a subject suffering from a disease or condition, the method comprising: a) preparation of an adhesive composition comprising a multivalent metal salt and a compound of Formula (I) (e.g., a small organic phosphate compound) in an aqueous solution or suspension; and b) applying the composition to the desired region; wherein the composition hardens and/or cures in less than about 30 minutes (e.g., less than about 25 minutes, about 20 minutes, about 15 minutes, about 12 minutes, about 10 minutes, about 8 minutes, about 7 minutes, about 6 minutes, about 5 minutes, or less). In some embodiments, the disease or condition comprises cancer (e.g., osteosarcoma), osteoporosis, rickets, osteogenesis imperfecta, fibrous dysplasia, Paget's disease of the bone, hearing loss, renal osteodystrophy, a malignancy of the bone, infection of the bone, osteonecrosis, or other genetic or developmental disease. In some embodiments, the disease or disorder comprises fibrous dysplasia or nerve compression. In some embodiments, the subject is suffering from or has been diagnosed with decay, fracture, abfraction, attrition, or erosion of teeth.

In some embodiments, the disclosure features a method of repairing a bone defect in a subject caused by a trauma, the method comprising: a) preparing an adhesive composition comprising a multivalent metal salt and a compound of Formula (I) (e.g., a small organic phosphate compound) compound in an aqueous solution or suspension; and b) applying the composition to the desired region; wherein the composition hardens and/or cures in less than about 30 minutes (e.g., less than about 25 minutes, about 20 minutes, about 15 minutes, about 12 minutes, about 10 minutes, about 8 minutes, about 7 minutes, about 6 minutes, about 5 minutes, or less).

In some embodiments, the disclosure features a method of preparing a graft of bone tissue or composite of bone and hardened composition, the method comprising: a) preparing an adhesive composition comprising a multivalent metal salt and a compound of Formula (I) (e.g., a small organic phosphate compound) in an aqueous solution or suspension; b) applying the composition to the desired region; c) forming the composition to a desired shape and size, wherein the composition hardens and/or cures in less than about 30 minutes (e.g., less than about 25 minutes, about 20 minutes, about 15 minutes, about 12 minutes, about 10 minutes, about 8 minutes, about 7 minutes, about 6 minutes, about 5 minutes, or less); and d) harvesting the graft by removing the form composed of the bone or composite of bone and hardened composition.

In some embodiments, the disclosure features a method of preparing a graft of bone tissue or composite of bone and hardened composition, the method comprising: a) preparing an adhesive composition comprising a multivalent metal salt and a compound of Formula (I) (e.g., a small organic phosphate compound) in an aqueous solution or suspension; b) forming the composition to a desired shape and size; c) application of the form to the desired region of bone, wherein the composition hardens and/or cures in less than about 30 minutes (e.g., less than about 25 minutes, about 20 minutes, about 15 minutes, about 12 minutes, about 10 minutes, about 8 minutes, about 7 minutes, about 6 minutes, about 5 minutes, or less); and d) harvesting the graft by removing the form composed of the bone or composite of bone and hardened composition. In some embodiments, the form adhesively applied might be shaped to conform with a plan based on observation and measurement of radiographic images or data.

In some embodiments, the disclosure features a method of preparing a graft of bone tissue or composite of bone and hardened composition, the method comprising: a) preparing an adhesive composition comprising a multivalent metal salt and a compound of Formula (I) (e.g., a small organic phosphate compound) in an aqueous solution or suspension, wherein the composition hardens and/or cures in less than about 30 minutes (e.g., less than about 25 minutes, about 20 minutes, about 15 minutes, about 12 minutes, about 10 minutes, about 8 minutes, about 7 minutes, about 6 minutes, about 5 minutes, or less); b) forming the composition to a desired shape and size; c) exposing the formed composition to tissue culture capable of remodeling the form to bone tissue; and d) harvesting the graft form composed of the bone or composite of bone and hardened composition. In some embodiments, the form might be shaped to conform with a plan based on observation and measurement of radiographic images or data.

In some embodiments, the disclosure features a method of adhesively repairing defects and fractures, and adhesively joining bony segments in non-human vertebrate animals, the method comprising: a) preparing an adhesive composition comprising a multivalent metal salt and a compound of Formula (I) (e.g., a small organic phosphate compound) in an aqueous solution or suspension; and b) applying the composition to the desired region; wherein the composition hardens and/or cures in less than about 30 minutes (e.g., less than about 25 minutes, about 20 minutes, about 15 minutes, about 12 minutes, about 10 minutes, about 8 minutes, about 7 minutes, about 6 minutes, about 5 minutes, or less).

In some embodiments, the disclosure features a method of adhesively repairing defects and fractures, and adhesively joining segments in non-vertebrate animal structures (e.g., corals), the method comprising: a) preparing an adhesive composition comprising a multivalent metal salt a compound of Formula (I) (e.g., a small organic phosphate compound) in an aqueous solution or suspension; and b) applying the composition to the desired region; wherein the composition hardens and/or cures in less than about 30 minutes (e.g., less than about 25 minutes, about 20 minutes, about 15 minutes, about 12 minutes, about 10 minutes, about 8 minutes, about 7 minutes, about 6 minutes, about 5 minutes, or less).

In some embodiments, the disclosure features a method of repairing a gap or space between articulating bone surfaces (e.g., facet joints) or a method of bridging a gap space between bone surfaces (e.g., between vertebral bodies, between transverse processes, between spinous processes) to prevent relative displacement of the bone surfaces (e.g. spinal fusion procedures) and to provide load bearing support with or without supportive implants devices (e.g., screws, plates, interbody cages). These applications might be made singly or to provide multipoint fixation when applied in several of the above or other, loci. In some embodiments, the method comprises: a) preparing an adhesive composition comprising a multivalent metal salt and a compound of Formula (I) (e.g., a small organic phosphate compound) in an aqueous solution or suspension; and b) applying the composition to the desired region with or without the use of supportive implant devices; wherein the composition hardens and/or cures in less than about 30 minutes (e.g., less than about 25 minutes, about 20 minutes, about 15 minutes, about 12 minutes, about 10 minutes, about 8 minutes, about 7 minutes, about 6 minutes, about 5 minutes, or less).

In some embodiments, the multivalent metal salt comprises calcium. In some embodiments, the multivalent metal salt comprises calcium and/or phosphate. In some embodiments, the multivalent metal salt comprises hydroxyapatite. In some embodiments, the multivalent metal salt comprises tricalcium phosphate. In some embodiments, the tricalcium phosphate comprises either alpha tricalcium phosphate or beta tricalcium phosphate. In some embodiments, the multivalent metal salt comprises an oxide. In some embodiments, the multivalent metal salt comprises calcium oxide. In some embodiments, the multivalent metal salt comprises tricalcium phosphate and calcium oxide. In some embodiments, the multivalent metal salt does not comprise tetracalcium phosphate.

In some embodiments, the multivalent metal salt is a multivalent calcium compound. In some embodiments, the multivalent calcium compound comprises tetracalcium phosphate. In some embodiments, the composition comprises a plurality of multivalent calcium compounds. In some embodiments, the plurality comprises tetracalcium phosphate and at least one other multivalent calcium compound. In some embodiments, the multivalent calcium compound does not comprise tetracalcium phosphate.

The amount of a multivalent metal salt (e.g., a calcium phosphate or calcium oxide or a combination thereof) in the composition may vary, e.g., between about 10% to about 90 weight by weight (w/w) of the total composition. In some embodiments, the amount of the multivalent metal salt (e.g., a calcium phosphate or calcium oxide or a combination thereof) is in the range of about 10% to about 90%, about 15% to about 85%, about 20% to about 80%, about 30% to about 75%, about 40% to about 70%, or about 50% to about 65% w/w of the total composition. In other embodiments, the amount of the metal salt (e.g., a calcium phosphate or calcium oxide or a combination thereof) is in the range of about 5% to about 95%, about 10% to about 85%, about 15% to about 75%, about 20% to about 65%, about 25% to about 55%, or about 35% to about 50% w/w of the total composition.

In any and all aspects and embodiments herein, the small organic phosphate may be a compound of Formula (I-a) or a salt thereof:

Formula (I-a)

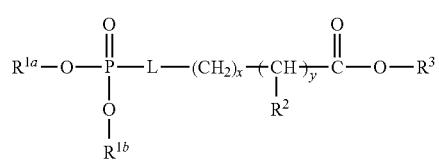

wherein L is O, S, or NH; each of $R^{1a}$ and $R^{1b}$ is independently H, optionally substituted alkyl, or optionally substituted aryl; $R^2$ is H, $NR^{4a}R^{4b}$, $C(O)R^5$, or $C(O)OR^5$; $R^3$ is independently H, optionally substituted alkyl, or optionally substituted aryl; each of $R^{4a}$ and $R^{4a}$ is independently H, $C(O)R^6$, or optionally substituted alkyl; $R^5$ is H, optionally substituted alkyl, or optionally substituted aryl; $R^6$ is optionally substituted alkyl or optionally substituted aryl; and each of x and y is independently 0, 1, 2, or 3.

In some embodiments, L is O or S. In some embodiments, L is O. In some embodiments, each of $R^{1a}$ and $R^{1b}$ is independently H. In some embodiments, L is O and each of $R^{1a}$ and $R^{1b}$ is independently H. In some embodiments, $R^2$ is H, $NR^{4a}R^{4b}$ or $C(O)R^5$. In some embodiments, $R^2$ is $NR^{4a}R^{4b}$. In some embodiments, $R^2$ is $NR^{4a}R^{4b}$ and each of $R^{4a}$ and $R^{4b}$ is independently H. In some embodiments, L is O, each of $R^{1a}$ and $R^{1b}$ is H, $R^2$ is $NR^{4a}R^{4b}$, and each of $R^{4a}$ and $R^{4b}$ is independently H. In some embodiments, $R^3$ is H. In some embodiments, L is O, each of $R^{1a}$ and $R^{1b}$ is independently H, $R^2$ is $NR^{4a}R^{4b}$ each of $R^{4a}$ and $R^{4b}$ is independently H, and $R^3$ is H. In some embodiments, each of x and y is 0 or 1. In some embodiments, each of x and y is 1. In some embodiments, L is O, each of $R^{1a}$ and $R^{1b}$ is H, $R^2$ is $NR^{4a}R^{4b}$ each of $R^{4a}$ and $R^{4b}$ is independently H, $R^3$ is H, and each of x and y is 1. In some embodiments, the compound of Formula (I-a) is phosphoserine.

In another aspect, the disclosure features an adhesive composition comprising a mixture of at least two multivalent metal salts and a compound of Formula (I) or a salt thereof in an aqueous solution or suspension:

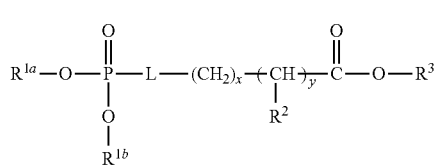

(I)

wherein L is O, S, NH, or $CH_2$; each of $R^{1a}$ and $R^{1b}$ is independently H, optionally substituted alkyl, or optionally substituted aryl; $R^2$ is H, $NR^{4a}R^{4b}$ $C(O)R^5$, or $C(O)OR^5$; $R^3$ is independently H, optionally substituted alkyl, or optionally substituted aryl; each of $R^{4a}$ and $R^{4a}$ is independently H, $C(O)R^6$, or optionally substituted alkyl; $R^5$ is H, optionally substituted alkyl, or optionally substituted aryl; $R^6$ is optionally substituted alkyl or optionally substituted aryl; and each of x and y is independently 0, 1, 2, or 3.

In some embodiments, L is O or S. In some embodiments, L is O. In some embodiments, each of $R^{1a}$ and $R^{1b}$ is independently H. In some embodiments, L is O and each of $R^{1a}$ and $R^{1b}$ is independently H. In some embodiments, $R^2$ is H, $NR^{4a}R^{4b}$ or $C(O)R^5$. In some embodiments, $R^2$ is $NR^{4a}R^{4b}$. In some embodiments, $R^2$ is $NR^{4a}R^{4b}$ and each of $R^{4a}$ and $R^{4b}$ is independently H. In some embodiments, L is O, each of $R^{1a}$ and $R^{1b}$ is H, $R^2$ is $NR^{4a}R^{4b}$, and each of $R^{4a}$ and $R^{4b}$ is independently H. In some embodiments, $R^3$ is H. In some embodiments, L is O, each of $R^{1a}$ and $R^{1b}$ is independently H, $R^2$ is $NR^{4a}R^{4b}$, each of $R^{4a}$ and $R^{4b}$ is independently H, and $R^3$ is H. In some embodiments, each of x and y is 0 or 1. In some embodiments, each of x and y is 1. In some embodiments, L is O, each of $R^{1a}$ and $R^{1b}$ is H, $R^2$ is $NR^{4a}R^{4b}$, each of $R^{4a}$ and $R^{4b}$ is independently H, $R^3$ is H, and each of x and y is 1. In some embodiments, the compound of Formula (I) is phosphoserine.

In some embodiments, the multivalent metal salts comprise calcium. In some embodiments, at least one of the multivalent metal salts comprise calcium and phosphate. In some embodiments, at least one of the multivalent metal salts comprises hydroxyapatite. In some embodiments, at least one of the multivalent metal salts comprises tricalcium phosphate. In some embodiments, the tricalcium phosphate comprises either alpha tricalcium phosphate or beta tricalcium phosphate. In some embodiments, at least one of the multivalent metal salts comprises an oxide. In some embodiments, at least one of the multivalent metal salts is calcium oxide. In some embodiments, the composition comprises tricalcium phosphate and calcium oxide. In some embodiments, the composition does not contain tetracalcium phosphate.

In some embodiments, each of the at least two multivalent metal salts is present in the composition from about 10% to about 90% weight by weight (w/w) of the total composition (e.g., from about 10% to about 90%, about 15% to about 85%, about 20% to about 80%, about 25% to about 75%, about 30% to about 70%, about 30% to about 65%, about 35% to about 60%). %). In some embodiments, the composition comprises hydroxyapatite, and the hydroxyapatite is present in the composition from about 10% to about 90% weight by weight (w/w) of the total composition (e.g., from about 10% to about 90%, about 15% to about 85%, about 20% to about 80%, about 25% to about 75%, about 30% to about 70%, about 30% to about 65%, about 35% to about 60%). In some embodiments, the composition comprises tricalcium phosphate, and the tricalcium phosphate is present in the composition from about 10% to about 90% weight by weight (w/w) of the total composition (e.g., from about 10% to about 90%, about 15% to about 85%, about 20% to about 80%, about 25% to about 75%, about 30% to about 70%, about 30% to about 65%, about 35% to about 60%). In some embodiments, the composition comprises calcium oxide, and the calcium oxide is present from about 1% to about 30% weight by weight (w/w) of the total composition (e.g., from about 1% to about 30%, about 1% to about 10%, about 1% to about 5%, about 5% to about 20%, about 5% to about 15%, about 5% to about 10%, about 10% to about 20%, about 10% to about 15%).

In some embodiments, the aqueous solution or suspension comprises water, saliva, saline, serum, plasma, or blood. In some embodiments, the aqueous solution or suspension comprises saliva, serum, or blood.

In some embodiments, the multivalent metal salt is initially provided as granules or a powder. In some embodiments, the composition further comprises an additive.

In another aspect, the disclosure features a method for fixation of a structure to a bone, the method comprising preparation and use of an adhesive composition comprising at least two multivalent metal salts and a compound of Formula (I) or a salt thereof:

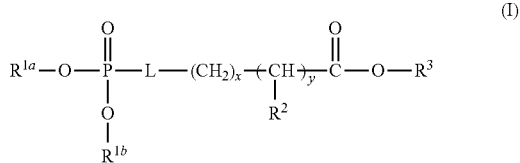

(I)

wherein L is O, S, NH, or $CH_2$; each of $R^{1a}$ and $R^{1b}$ is independently H, optionally substituted alkyl, or optionally substituted aryl; $R^2$ is H, $NR^{4a}R^{4b}$, $C(O)R^5$, or $C(O)OR^5$; $R^3$ is H, optionally substituted alkyl, or optionally substituted aryl; each of $R^{4a}$ and $R^{4a}$ is independently H, $C(O)R^6$, or optionally substituted alkyl; $R^5$ is H, optionally substituted alkyl, or optionally substituted aryl; $R^6$ is optionally substituted alkyl or optionally substituted aryl; and each of x and y is independently 0, 1, 2, or 3; in an aqueous solution or suspension to thereby fix the structure to the bone.

In some embodiments, L is O or S. In some embodiments, L is O. In some embodiments, each of $R^{1a}$ and $R^{1b}$ is independently H. In some embodiments, L is O and each of $R^{1a}$ and $R^{1b}$ is independently H. In some embodiments, $R^2$ is H, $NR^{4a}R^{4b}$ or $C(O)R^5$. In some embodiments, $R^2$ is $NR^{4a}R^{4b}$. In some embodiments, $R^2$ is $NR^{4a}R^{4b}$ and each of $R^{4a}$ and $R^{4b}$ is independently H. In some embodiments, L is O, each of $R^{1a}$ and $R^{1b}$ is H, $R^2$ is $NR^{4a}R^{4b}$, and each of $R^{4a}$ and $R^{4b}$ is independently H. In some embodiments, $R^3$ is H. In some embodiments, L is O, each of $R^{1a}$ and $R^{1b}$ is independently H, $R^2$ is $NR^{4a}R^{4b}$ each of $R^{4a}$ and $R^{4b}$ is independently H, and $R^3$ is H. In some embodiments, each of x and y is 0 or 1. In some embodiments, each of x and y is 1. In some embodiments, L is O, each of $R^{1a}$ and $R^{1b}$ is H, $R^2$ is $NR^{4a}$ is $NR^{4a}R^{4b}$, each of $R^{4a}$ and $R^{4b}$ is independently H, $R^3$ is H, and each of x and y is 1. In some embodiments, the compound of Formula (I) is phosphoserine.

In some embodiments, the multivalent metal salts comprise calcium. In some embodiments, at least one of the multivalent metal salts comprises calcium and phosphate. In some embodiments, at least one of the multivalent metal salts comprises tricalcium phosphate. In some embodiments, the tricalcium phosphate comprises either alpha tricalcium phosphate or beta tricalcium phosphate. In some embodiments, at least one of the multivalent metal salts comprises an oxide. In some embodiments, at least one of the multivalent metal salts comprises calcium oxide. In some embodiments, the composition comprises tricalcium phosphate and calcium oxide. In some embodiments, the composition does not contain tetracalcium phosphate.

In some embodiments, each of the at least two multivalent metal salts is present in the composition from about 10% to about 90% weight by weight (w/w) of the total composition (e.g., from about 10% to about 90%, about 15% to about 85%, about 20% to about 80%, about 25% to about 75%, about 30% to about 70%, about 30% to about 65%, about 35% to about 60%). In some embodiments, the composition comprises tricalcium phosphate, and the tricalcium phosphate is present in the composition from about 10% to about 90% weight by weight (w/w) of the total composition (e.g., from about 10% to about 90%, about 15% to about 85%, about 20% to about 80%, about 25% to about 75%, about 30% to about 70%, about 30% to about 65%, about 35% to about 60%). In some embodiments, the composition comprises calcium oxide, and the calcium oxide is present from about 1% to about 30% weight by weight (w/w) of the total composition (e.g., from about 1% to about 30%, about 1% to about 10%, about 1% to about 5%, about 5% to about 20%, about 5% to about 15%, about 5% to about 10%, about 10% to about 20%, about 10% to about 15%.

In some embodiments, the aqueous solution or suspension comprises water, saliva, saline, serum, plasma, or blood. In some embodiments, the aqueous solution or suspension comprises saliva, serum, or blood.

In some embodiments, the multivalent metal salt is initially provided as granules or a powder. In some embodiments, the composition further comprises an additive.

In yet another aspect, the disclosure features a method of filling a void or gap in a bone, the method comprising preparation and use of an adhesive composition comprising at least two multivalent metal salts and a compound of Formula (I) or a salt thereof:

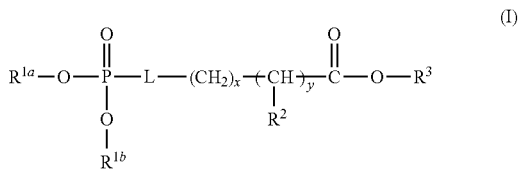

wherein L is O, S, NH, or $CH_2$; each of $R^{1a}$ and $R^{1b}$ is independently H, optionally substituted alkyl, or optionally substituted aryl; $R^2$ is H, $NR^{4a}R^{4b}$, $C(O)R^5$, or $C(O)OR^5$; $R^3$ is H, optionally substituted alkyl, or optionally substituted aryl; each of $R^{4a}$ and $R^{4a}$ is independently H, $C(O)R^6$, or optionally substituted alkyl; $R^5$ is H, optionally substituted alkyl, or optionally substituted aryl; $R^6$ is optionally substituted alkyl or optionally substituted aryl; and each of x and y is independently 0, 1, 2, or 3; in an aqueous solution or suspension to thereby fill the void or gap in the bone.

In some embodiments, L is O or S. In some embodiments, L is O. In some embodiments, each of $R^{1a}$ and $R^{1b}$ is independently H. In some embodiments, L is O and each of $R^{1a}$ and $R^{1b}$ is independently H. In some embodiments, $R^2$ is H, $NR^{4a}R^{4b}$ or $C(O)R^5$. In some embodiments, $R^2$ is $NR^{4a}R^{4b}$. In some embodiments, $R^2$ is $NR^{4a}R^{4b}$ and each of $R^{4a}$ and $R^{4b}$ is independently H. In some embodiments, L is O, each of $R^{1a}$ and $R^{1b}$ is H, $R^2$ is $NR^{4a}R^{4b}$ and each of $R^{4a}$ and $R^{4b}$ is independently H. In some embodiments, $R^3$ is H. In some embodiments, L is O, each of $R^{1a}$ and $R^{1b}$ is independently H, $R^2$ is $NR^{4a}R^{4b}$ each of $R^{4a}$ and $R^{4b}$ is independently H, and $R^3$ is H. In some embodiments, each of x and y is 0 or 1. In some embodiments, each of x and y is 1. In some embodiments, L is O, each of $R^{1a}$ and $R^{1b}$ is H, $R^2$ is each of $R^{4a}$ and $R^{4b}$ is independently H, $R^3$ is H, and each of x and y is 1. In some embodiments, the compound of Formula (I) is phosphoserine.

In some embodiments, the multivalent metal salts comprise calcium. In some embodiments, at least one of the multivalent metal salts comprise calcium and phosphate. In some embodiments, at least one of the multivalent metal salts comprises tricalcium phosphate. In some embodiments, the tricalcium phosphate comprises either alpha tricalcium phosphate or beta tricalcium phosphate. In some embodiments, at least one of the multivalent metal salts comprises an oxide. In some embodiments, at least one of the multivalent metal salts is calcium oxide. In some embodiments, the composition comprises tricalcium phosphate and calcium oxide. In some embodiments, the composition does not contain tetracalcium phosphate.

In some embodiments, each of the at least two multivalent metal salts is present in the composition from about 10% to about 90% weight by weight (w/w) of the total composition (e.g., from about 10% to about 90%, about 15% to about 85%, about 20% to about 80%, about 25% to about 75%, about 30% to about 70%, about 30% to about 65%, about 35% to about 60%). In some embodiments, the composition comprises tricalcium phosphate, and the tricalcium phosphate is present in the composition from about 10% to about 90% weight by weight (w/w) of the total composition (e.g., from about 10% to about 90%, about 15% to about 85%, about 20% to about 80%, about 25% to about 75%, about 30% to about 70%, about 30% to about 65%, about 35% to about 60%). In some embodiments, the composition comprises hydroxyapatite, and the tricalcium phosphate is present in the composition from about 10% to about 90% weight by weight (w/w) of the total composition (e.g., from about 10% to about 90%, about 15% to about 85%, about 20% to about 80%, about 25% to about 75%, about 30% to about 70%, about 30% to about 65%, about 35% to about 60%). In some embodiments, the composition comprises calcium oxide, and the calcium oxide is present from about 1% to about 30% weight by weight (w/w) of the total composition (e.g., from about 1% to about 30%, about 1% to about 10%, about 1% to about 5%, about 5% to about 20%, about 5% to about 15%, about 5% to about 10%, about 10% to about 15%).

In some embodiments, the aqueous solution or suspension comprises water, saliva, saline, serum, plasma, or blood. In some embodiments, the aqueous solution or suspension comprises saliva, serum, or blood.

In some embodiments, the multivalent metal salt is initially provided as granules or a powder. In some embodiments, the composition further comprises an additive.

In another aspect, the present disclosure features a kit for fixation of a structure to a bone comprising a container (e.g., a first container) containing a composition comprising at least one multivalent metal salt (e.g., at least two multivalent metal salts) and a compound of Formula (I) or a salt thereof:

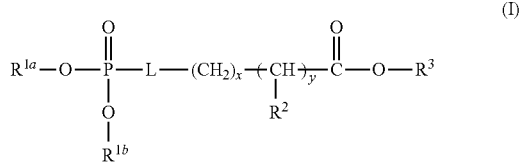

wherein L is O, S, NH, or CH$_2$; each of R$^{1a}$ and R$^{1b}$ is independently H, optionally substituted alkyl, or optionally substituted aryl; R$^2$ is H, NR$^{4a}$R$^{4b}$, C(O)R$^5$, or C(O)OR$^5$; R$^3$ is H, optionally substituted alkyl, or optionally substituted aryl; each of R$^{4a}$ and R$^{4a}$ is independently H, C(O)R$^6$, or optionally substituted alkyl; R$^5$ is H, optionally substituted alkyl, or optionally substituted aryl; R$^6$ is optionally substituted alkyl or optionally substituted aryl; and each of x and y is independently 0, 1, 2, or 3. In some embodiments, the kit further comprises a second container containing an aqueous medium.

In another aspect, the present disclosure features a kit for filling a void or gap in a bone comprising a container (e.g., a first container) containing a composition comprising at least one multivalent metal salt (e.g., at least two multivalent metal salts) and a compound of Formula (I) or a salt thereof:

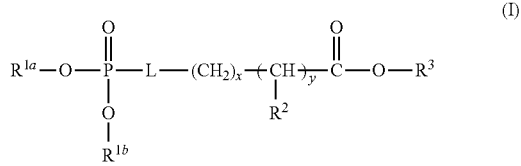

wherein L is O, S, NH, or CH$_2$; each of R$^{1a}$ and R$^{1b}$ is independently H, optionally substituted alkyl, or optionally substituted aryl; R$^2$ is H, NR$^{4a}$R$^{4b}$, C(O)R$^5$, or C(O)OR$^5$; R$^3$ is H, optionally substituted alkyl, or optionally substituted aryl; each of R$^{4a}$ and R$^{4a}$ is independently H, C(O)R$^6$, or optionally substituted alkyl; R$^5$ is H, optionally substituted alkyl, or optionally substituted aryl; R$^6$ is optionally substituted alkyl or optionally substituted aryl; and each of x and y is independently 0, 1, 2, or 3. In some embodiments, the kit further comprises a second container containing an aqueous medium.

In another aspect, the present disclosure features a kit for increasing the volume of a bone comprising a container (e.g., a first container) containing a composition comprising at least one multivalent metal salt (e.g., at least two multivalent metal salts) and a compound of Formula (I) or a salt thereof:

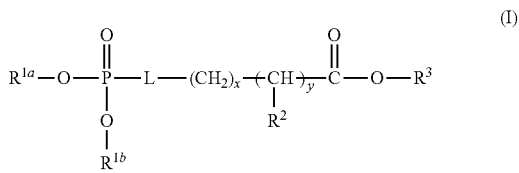

wherein L is O, S, NH, or CH$_2$; each of R$^{1a}$ and R$^{1b}$ is independently H, optionally substituted alkyl, or optionally substituted aryl; R$^2$ is H, NR$^{4a}$R$^{4b}$, C(O)R$^5$, or C(O)OR$^5$; R$^3$ is H, optionally substituted alkyl, or optionally substituted aryl; each of R$^{4a}$ and R$^{4a}$ is independently H, C(O)R$^6$, or optionally substituted alkyl; R$^5$ is H, optionally substituted alkyl, or optionally substituted aryl; R$^6$ is optionally substituted alkyl or optionally substituted aryl; and each of x and y is independently 0, 1, 2, or 3. In some embodiments, the kit further comprises a second container containing an aqueous medium.

In some embodiments of the above aspects, the multivalent salt comprises calcium. In some embodiments, the multivalent metal salt comprises calcium and phosphate. In some embodiments, the multivalent salt comprises tetracalcium phosphate. In some embodiments, the multivalent salt does not comprise tetracalcium phosphate. In some embodiments, the multivalent salt comprises tricalcium phosphate. In some embodiments, the tricalcium phosphate comprises either alpha tricalcium phosphate or beta tricalcium phosphate. In some embodiments, the multivalent metal salt comprises an oxide. In some embodiments, the multivalent metal salt comprises calcium oxide. In some embodiments, the multivalent salt comprises hydroxyapatite.

In some embodiments, the compound of Formula (I) is phosphoserine.

In some embodiments, the aqueous medium comprises water or saline (e.g., phosphate buffered saline). In some embodiments, the aqueous medium comprises water, saliva, saline, serum, plasma, or blood. In some embodiments, the aqueous solution or suspension comprises saliva, serum, or blood. In some embodiments, the aqueous medium is not provided as part of the kit. In some embodiments, the aqueous medium is present at the site of application of the composition.

In some embodiments, the first container further comprises an additive.

In some embodiments, the kit consists of a single container (e.g., a first container, e.g., comprising at least one multivalent metal salt and a compound of Formula (I) or a salt thereof). In some embodiments, the kit comprises a first container (e.g., comprising at least one multivalent metal salt and a compound of Formula (I) or a salt thereof) and a second container (e.g., comprising an aqueous medium).

In some embodiments, upon mixing the contents of the first container with the contents of the second container, the resulting composition comprises an adhesive strength greater than about 1 MPa (e.g, greater than about 1.5 MPa, about 2.0 MPa, about 2.5 MPa, or about 3 MPa) upon hardening or curing. In some embodiments, the hardening or curing occurs within at least about 30 minutes (e.g., within at least about 25 minutes, about 20 minutes, about 15 minutes, about 12 minutes, about 10 minutes, about 8 minutes, or about 5 minutes) after mixing the contents of the first container with the contents of the second container.

BRIEF DESCRIPTION OF DRAWINGS

FIG. 22 is a cross section view of a prosthetic limb attachment to an amputation bone stump inserted into the medullary space of a long bone (e.g. femur) and stabilized for load bearing support through application of an exemplary adhesive composition to fill space between surfaces of prosthetic limb attachment device and the adjacent surfaces of bone. Highlighted in the drawing is the seal provided by the adhesive composition.

FIG. 23 shows two images depicting the response to exemplary adhesive Composition A in an alveolus at 3 weeks post-operation (FIG. 23A, 20× magnification; detail in FIG. 23B, 100× magnification.

FIG. 24 shows three images depicting the response to exemplary adhesive Composition C in an alveolus at 21 weeks post-operation (FIG. 24A, 25× magnification;

FIG. 24B, 100× magnification; FIG. 24C, 400× magnification.

FIGS. 27A-B are images of a cemented implant in an oversized osteotomy and the response to a cemented exemplary adhesive Composition C (50× magnification)

FIG. 28 are a series of CBCT images depicting the response of exemplary adhesive Composition F as an onlay graft near cuspid from directly after operation (FIG. 28A) through 1 week (FIG. 28B), 2 weeks (FIG. 28C), 3 weeks (FIG. 28D), 4 weeks (FIG. 28E), 8 weeks (FIG. 28F), and 10 Weeks (FIG. 28G).

FIG. 29 are a series of images depicting the response to exemplary adhesive Composition F as an onlay graft near cuspid at 9 weeks post-operative. A clinical image is shown in FIG. 29A, a 3D CBCT image in FIG. 29B, and a CBCT image of the parapalatal plane in FIG. 29C.

FIG. 30 is an image of explanted spinal tissue from a rabbit spine mounted on an Instron during a tensile test. Adjacent rabbit spinal vertebral bodies (L5/L6) were fixated with exemplary adhesive Composition G to bridge the gap between transverse processes (bilateral).

FIG. 32 shows three time course radiographic images of spinal fusion obtained from adjacent rabbit spinal vertebral bodies (L5/L6) fixated with exemplary adhesive Composition G to bridge the gap between transverse processes (bilateral). FIG. 32A is a post-operative CBCT image, while FIG. 32B is a CBCT image at 3 weeks and FIG. 32C is a 3D rendering of this FIG. 32B.

DETAILED DESCRIPTION

Figure 1:
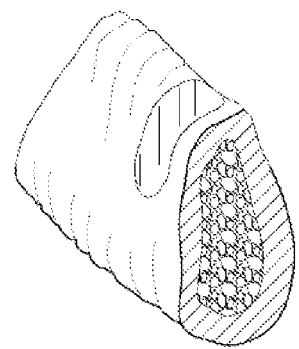
FIG. 1 is a drawing showing an exemplary tooth extraction site in the mandible highlighting the alveolar ridge with dehiscent lateral bone. The state of the alveolar ridge in its clinically presenting state or after site has been prepared (by, e.g., milling, drilling, reaming) is shown, ready to accept an adhesive composition.

Embodiments of this disclosure feature adhesive compositions comprising a multivalent metal salt and a small organic phosphate compound as well as methods of use thereof. More specifically, the disclosure applies to adhesive compositions and their use to attach structures to the bony skeleton, wherein said structures include bone, calcified tissues, grafts, implants, and devices.

Components of the Adhesive Compositions

Multivalent metal salts (e.g., tetracalcium phosphate) have been shown to react with small organic phosphate compounds in aqueous environments to form compositions with powerful adhesive properties. Without wishing to be bound by theory, these multivalent metal salts are thought to form ionic interactions with organic phosphate compounds, which when combined in certain ratios react in an exothermic fashion to provide a cement-like material. Exemplary multivalent metal salts may be organic or inorganic in nature and include calcium phosphates (e.g., hydroxyapatite, octacalcium phosphate, tetracalcium phosphate, tricalcium phosphate), calcium nitrate, calcium citrate, calcium carbonate, magnesium phosphates, sodium silicates, lithium phosphates, titanium phosphates, strontium phosphates, barium phosphates, zinc phosphates, calcium oxide, magnesium oxide, and combinations thereof.

The amount of a multivalent metal salt (e.g., a calcium phosphate or calcium oxide or a combination thereof) may vary, e.g., between about 10% to about 90 weight by weight (w/w) of the total composition. In some embodiments, the amount of the multivalent metal salt (e.g., a calcium phosphate or calcium oxide or a combination thereof) is in the range of about 10% to about 90%, about 15% to about 85%, about 20% to about 80%, about 30% to about 75%, about 40% to about 70%, or about 50% to about 65% w/w of the total composition. In other embodiments, the amount of the metal salt (e.g., a calcium phosphate or calcium oxide or a combination thereof) is in the range of about 5% to about 95%, about 10% to about 85%, about 15% to about 75%, about 20% to about 65%, about 25% to about 55%, or about 35% to about 50% w/w of the total composition. In some embodiments, the total combined amount of each multivalent salt (e.g., a calcium phosphate or calcium oxide or a combination thereof) may vary, e.g., between about 10% to about 90 weight by weight (w/w) of the total composition.

In some embodiments, the multivalent metal salt comprises calcium. In some embodiments, the multivalent metal salt comprises calcium and phosphate. In some embodiments, the multivalent metal salt comprises tetracalcium phosphate. In some embodiments, the composition comprises a plurality of multivalent metal salt compounds. In some embodiments, the plurality comprises tetracalcium phosphate and at least one other multivalent metal salt compound. In some embodiments, the multivalent metal salt comprises hydroxyapatite. In some embodiments, the multivalent metal salts comprise tricalcium phosphate. In some embodiments, the tricalcium phosphate comprises either alpha tricalcium phosphate or beta tricalcium phosphate. In some embodiments, the multivalent metal salt comprises an oxide. In some embodiments, the multivalent metal salt is calcium oxide. In some embodiments, the multivalent metal salt compound does not comprise tetracalcium phosphate. In some embodiments, the composition comprises tricalcium phosphate and calcium oxide.

The present disclosure features an adhesive composition comprising a multivalent metal salt and a compound of Formula (I) or a salt thereof:

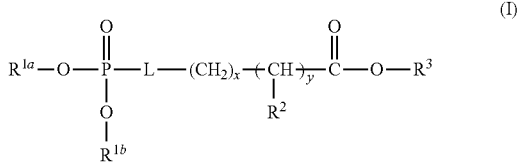

wherein L is O, S, NH, or $CH_2$; each of $R^{1a}$ and $R^{1b}$ is independently H, optionally substituted alkyl, or optionally substituted aryl; $R^2$ is H, $NR^{4a}R^{4b}$, $C(O)R^5$, or $C(O)OR^5$; $R^3$ is H, optionally substituted alkyl, or optionally substituted aryl; each of $R^{4a}$ and $R^{4a}$ is independently H, $C(O)R^6$, or optionally substituted alkyl; $R^5$ is H, optionally substituted alkyl, or optionally substituted aryl; $R^6$ is optionally substituted alkyl or optionally substituted aryl; and each of x and y is independently 0, 1, 2, or 3.

In some embodiments, L is O or S. In some embodiments, L is O. In some embodiments, each of $R^{1a}$ and $R^{1b}$ is independently H. In some embodiments, L is O and each of $R^{1a}$ and $R^{1b}$ is independently H. In some embodiments, $R^2$ is H, $NR^{4a}R^{4b}$, or $C(O)R^5$. In some embodiments, $R^2$ is $NR^{4a}R^{4b}$. In some embodiments, $R^2$ is $NR^{4a}R^{4b}$ and each of $R^{4a}$ and $R^{4b}$ is independently H. In some embodiments, L is O, each of $R^{1a}$ and $R^{1b}$ is H, $R^2$ is $NR^{4a}R^{4b}$, and each of $R^{4a}$ and $R^{4b}$ is independently H. In some embodiments, $R^3$ is H. In some embodiments, L is O, each of $R^{1a}$ and $R^{1b}$ is independently H, $R^2$ is $NR^{4a}R^{4b}$ each of $R^{4a}$ and $R^{4b}$ is independently H, and $R^3$ is H. In some embodiments, each of x and y is 0 or 1. In some embodiments, each of x and y is 1. In some embodiments, L is O, each of $R^{1a}$ and $R^{1b}$ is H, $R^2$ is each of $R^{4a}$ and $R^{4b}$ is independently H, $R^3$ is H, and each of x and y is 1. In some embodiments, the compound of Formula (I) comprises an organic phosphate compound (e.g., a small organic phosphate). In some embodiments, the compound of Formula (I) is phosphoserine.

As used herein, the term "optionally substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds (e.g., alkyl, alkenyl, alkynyl, cycloalkyl, heterocycloalkyl, aryl, or heteroaryl, any of which may itself be further substituted), as well as halogen, carbonyl (e.g., aldehyde, ketone, ester, carboxyl, or formyl), thiocarbonyl (e.g., thioester, thiocarboxylate, or thioformate), amino, $-N(R^b)(R^c)$, wherein each $R^b$ and $R^c$ is independently H or $C_1$-$C_6$ alkyl, cyano, nitro, $-SO_2N(R^b)(R^c)$, $-SOR^d$, and $S(O)_2R^d$, wherein each $R^b$, $R^c$, and $R^d$ is independently H or $C_1$-$C_6$ alkyl. Illustrative substituents include, for example, those described herein above. The permissible substituents can be one or more and the same or different for appropriate organic compounds. This disclosure is not intended to be limited in any manner by the permissible substituents of organic compounds. It will be further understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

In some embodiments, the molecular weight of a compound of Formula (I) is less than about 1000 g/mol. In some embodiments, the molecular weight of a compound of Formula (I) is between about 150 g/mol and about 1000 g/mol, e.g., between about 155 g/mol and about 750 g/mol, between about 160 g/mol and about 500 g/mol, between about 165 g/mol and about 250 g/mol, between about 170 g/mol and about 200 g/mol, or between about 175 g/mol and about 190 g/mol. In some embodiments, the molecular weight of a compound of Formula (I) is between about 180 g/mol and about 190 g/mol.

The compound of Formula (I) may adopt any stereoisomeric form or contain a mixture of stereoisomers. For example, compound of Formula (I) may be a mixture of D,L-phosphoserine, or contain substantially pure D-phosphoserine or substantially pure L-phosphoserine. In many embodiments, the stereochemistry of the compound of Formula (I) does not significantly impact the adhesive properties of the composition. In some embodiments, the particular stereochemistry of the compound of Formula (I) or the ratio of stereoisomers of compounds of Formula (I) has a significant impact on the adhesive properties of the composition.

The amount of a compound of Formula (I) may vary, e.g., between about 5% to about 95% w/w of the total composition. In some embodiments, the amount of the compound of Formula (I) is in the range of about 5% to about 80%, about 5% to about 50%, about 5% to about 30%, about 10% to about 80%, about 10% to about 50%, about 15% to about 40%, or about 20% to about 35% w/w of the total composition. In some embodiments, the compound of Formula (I) is a small organic phosphate (e.g., phosphoserine) and is present in the range of about 5% to about 80%, about 5% to about 50%, about 5% to about 30%, about 10% to about 80%, about 10% to about 50%, about 15% to about 40%, or about 20% to about 35% w/w of the total composition.

In other embodiments, the amount of a compound of Formula (I) may vary, e.g., between about 5% to about 95% w/w of the combined multivalent metal salt and a small organic phosphate compound. In some embodiments, the amount of the compound of Formula (I) is in the range of about 5% to about 80%, about 5% to about 50%, about 5% to about 30%, about 10% to about 80%, about 10% to about 50%, about 15% to about 40%, or about 20% to about 35% w/w of the combined multivalent metal salt compound of Formula (I). In some embodiments, the compound of Formula (I) is a small organic phosphate (e.g., phosphoserine) and is present in the range of about 5% to about 80%, about 5% to about 50%, about 5% to about 30%, about 10% to about 80%, about 10% to about 50%, about 15% to about 40%, or about 20% to about 35% w/w of the combined multivalent metal salt compound of Formula (I).

In some embodiments, the multivalent metal salt is present in the composition from about 10% to about 90% weight by weight (w/w) of the combined multivalent metal salt and the compound of Formula (I) (e.g., a small organic phosphate compound, e.g., phosphoserine). In some embodiments, the multivalent metal salt is present in the composition from about 10% to about 90%, about 15% to about 85%, about 20% to about 80%, about 25% to about 75%, about 30% to about 70%, about 30% to about 65%, about 45% to about 60%). In some embodiments, the composition comprises tetracalcium phosphate, and the tetracalcium phosphate is present in the composition from about 10% to about 90% weight by weight (w/w) of the combined multivalent metal salt and the compound of Formula (I) (e.g., a small organic phosphate compound, e.g., phosphoserine), e.g., from about 10% to about 90%, about 15% to about 85%, about 20% to about 80%, about 25% to about 75%, about 30% to about 70%, about 30% to about 65%, about 45% to about 60%. In some embodiments, the composition comprises tricalcium phosphate, and the tricalcium phosphate is present in the composition from about 10% to about 90% weight by weight (w/w) of the combined multivalent metal salt and the compound of Formula (I) (e.g., a small organic phosphate compound, e.g., phosphoserine), e.g., from about 10% to about 90%, about 15% to about 85%, about 20% to about 80%, about 25% to about 75%, about 30% to about 70%, about 30% to about 65%, about 45% to about 60%. In some embodiments, the composition comprises hydroxyapatite, and the hydroxyapatite is present from about 1% to about 50% weight by weight (w/w) of the combined multivalent metal salt and the compound of Formula (I) (e.g., a small organic phosphate compound, e.g., phosphoserine), e.g., from about 1% to about 30%, about 1% to about 15%, about 1% to about 5%, about 5% to about 10%, about 10% to about 15%, about 10% to about 20%, about 15% to about 25%. In some embodiments, the composition comprises calcium oxide, and the calcium oxide is present from about 1% to about 30% weight by weight (w/w) of the combined multivalent metal salt and the compound of Formula (I) (e.g., a small organic phosphate compound, e.g., phosphoserine), e.g., from about 1% to about 30%, about 1% to about 10%, about 1% to about 5%, about 5% to about 20%, about 5% to about 15%, about 5% to about 10%, about 10% to about 20%, about 10% to about 15). Each additive may additionally comprise phases and ingredients not specifically listed.

In some embodiments, the multivalent metal salt is initially provided as a powder or as a granule. These powders may exhibit a mean particle size of about 0.001 to about 0.250 mm, about 0.005 to about 0.150 mm, about 0.25005 to about 0.75075 mm, 0.25 to about 0.5010 to about 0.050 mm, about 0.015 to about 0.025 mm, about 0.020 to about 0.060 mm, about 0.020 to about 0.040 mm, about 0.040 to about 0.100 mm, about 0.040 to about 0.060 mm, about 0.060 to about 0.150 mm, or about 0.060 to about 0.125 mm. The mean particle size may be bi-modal to include any combination of mean particle sizes as previously described. These granules may exhibit a mean granule size of about 0.050 mm to about 5 mm, about 0.100 to about 1.500 mm, about 0.125 to 1.000 mm, 0.125 to 0.500 mm, about 0.125 to 0.250 mm, about 0.250 to 0.750 mm, about 0.250 to 0.500 mm, about 0.500 to 1.00 mm, about 0.500 to 0.750 mm. The mean granule size may be multi-modal to include any combination of mean granule sizes as previously described. The granules may be supplied with a various proportion of porosity and a various size of internal pores. In some embodiments, varying sizes of said powders or granules may be used in the adhesive composition.

In the present disclosure, the multivalent metal salts (e.g., calcium phosphates, calcium oxide or combinations thereof) react with the organic phosphate compounds to form an adhesive composition when combined with an aqueous medium. In some embodiments, the aqueous medium comprises water (e.g., sterile water), saliva, buffers (e.g., sodium phosphate, potassium phosphate, or saline (e.g., phosphate buffered saline)), increasing bone volume, blood-based solutions (e.g., plasma, serum, bone marrow), spinal fluid, dental pulp, cell-based solutions (e.g., solutions comprising fibroblasts, platelets, odontoblasts, stem cells (e.g., mesenchymal stem cells) histiocytes, macrophages, mast cells, or plasma cells), or combinations thereof in the form of aqueous solutions, suspensions, and colloids. In some embodiments, the aqueous medium comprises sterile water, distilled water, deionized water, sea water, or fresh water.

In some embodiments, the aqueous medium comprises water from the environment, e.g., fresh water, salt water or brackish water from the oceans, seas, bays, rivers, streams, ponds or other moving or standing water sources.

The amount of the aqueous medium mixed with the adhesive composition may vary, e.g., between about 5% to about 50% w/w of the total composition. In some embodiments, the amount of the aqueous medium is in the range of about 5% to about 50%, about 10% to about 35%, or about 15% to about 25% w/w of the total composition.

In some embodiments, the temperature of the aqueous medium can be controlled to affect the viscosity and setting kinetics of the adhesive composition (e.g., working time, setting time). Typically the temperature may be selected to range within room temperature (e.g., 15° C.-25° C., 18° C.-22° C.); however, the temperature may be selected to range from refrigerated temperatures (e.g., 2° C.-6° C.) to slow the setting kinetics to body temperature (e.g., 37° C.) to accelerate the setting kinetics.

In some embodiments, the method of applying the composition to a surface takes place in a dry or wet field. If a wet field is present, the adhesive composition may be applied without the pre-requisite removal of aqueous fluids (e.g., water, saline, cerebral spinal fluid, blood) from the surface. The adhesive composition can be applied in a wet field environment where the composition is subject to fluid pressure emanating from the surface (e.g., blood weeping from site of injury to bone, or cerebral spinal fluid flowing under pressure from ruptured dura mater and skull fracture) or fluid flow over surface so long as the initial tack strength is strong enough to resist loss of contact. The initial tack strength is established by making positive contact between the adhesive composition being applied and the surface to which it is intended to adhere. This can be accomplished either through application of the adhesive composition under hydrostatic pressure or through direct pressure of the material to the surface by application of compressive stress. In certain embodiments, it is possible to use the components without first combining them with an aqueous medium if the adhesive composition is to be used in an environment such that the aqueous medium is already present at the site of use. In this case, the composition can be spread on, sprayed on, or otherwise applied to the site of use and combined with the aqueous medium already present at said site.

In some embodiments, the compositions may further comprise an additive. An additive may be used to impart additional functionality to the composition of the disclosure, such as improving or affecting the handling, texture, durability, strength, or resorption rate of the material, or to provide additional cosmetic or medical properties. Exemplary additives may include salts (e.g., calcium carbonate, calcium bicarbonate, sodium carbonate, sodium bicarbonate, sodium chloride, potassium chloride), fillers, formulation bases, viscosity modifiers (e.g., polyols (e.g., glycerol, mannitol, sorbitol, trehalose, lactose, glucose, fructose, or sucrose)), abrasives (e.g., bone fragments), coloring agents (e.g., dyes, pigments, or opacifiers), flavoring agents (e.g., sweeteners), medications that act locally (e.g., anesthetics, coagulants, clotting factors, chemotactic agents, and agents inducing phenotypic change in local cells or tissues), medications that act systemically (e.g., analgesics, anticoagulants, hormones, vitamins, pain relievers, anti-inflammatory agents, chemotactic agents, or agents inducing phenotypic change in local cells or tissues), antimicrobial agents (e.g., antibacterial, antiviral, or antifungal agents) or combinations thereof. In some embodiments, the additive comprises a polymer. The biologically active substances (e.g., medicines) in the categories above might include active substances or precursors, which become biologically active upon modification after interaction with the surrounding environment. The substances might be synthetic, semisynthetic, or biologically derived (e.g., peptides, proteins, or small molecules). The substances might include, but not be limited to anti-inflammatories (e.g., steroids, nonsteroidal anti-inflammatory drugs, cyclooxygenase inhibitors), complement proteins, bone morphogenic factors and proteins, hormones active locally or systemically (e.g., parathyroid hormone, calcitocin), or other small molecules (e.g., calciferols).

In some embodiments, the additive is a polymer. Suitable polymers incorporated as additives into the adhesive composition may contain functional groups that contains electronegative atoms as the bonding sites of the polymer surfaces to the available metal ions, such as electronegative carbonyl oxygen atom(s) of the ester group or electronegative nitrogen atom(s) of the amine group as the bonding sites of the polymer surfaces to the available metal ions. These functional groups can be either in the backbone chain of the polymer or in groups pendant to the polymer chain. These polymeric based compounds may include, but are not limited to, one or more of the following; poly(L-lactide), poly(D,L-lactide), polyglycolide, poly(ε-caprolactone), poly(teramethylglycolic-acid), poly(dioxanone), poly(hydroxybutyrate), poly(hydroxyvalerate), poly(lactide-co-glycolide), poly(glycolide-co-trimethylene carbonate), poly(glycolide-co-caprolactone), poly(glycolide-co-dioxanone-co-trimethylene-carbonate), poly(tetramethylglycolic-acid-co-dioxanone-co-trimethylenecarbonate), poly(glycolide-co-caprolactone-co-lactide-co-trimethylene-carbonate), poly(hydroxybutyrate-co-hydroxyvalerate), poly(methylmethacrylate), poly(acrylate), polyamines, polyamides, polyimidazoles, poly(vinyl-pyrrolidone), collagen, silk, chitosan, hyaluronic acid, gelatin and/or mixtures thereof. In addition, copolymers of the above homopolymers also can be used.

The general structural nature of a polymer (e.g., a polymer used as an additive in an adhesive composition described herein) may include a linear homo and copolymer, a cross linked polymer, a block polymer, a branched polymer, a hyper branched polymer, or a star shaped polymer. The polymers can be added to the formulation in the form of a solution, powder, fiber, resin, liquid crystal, hydrogel, chip, flake, and the like. The polymeric material can be included directly within the adhesive composition or can be an adjunct that is applied in situ as the cement is applied to the bone.

In some embodiments, the composition comprises a plurality of said additives. In some embodiments, certain additives may be provided as powders or granules or solutes or any combination thereof. These powders may exhibit a mean particle size of about 0.001 to about 0.250 mm, about 0.005 to about 0.150 mm, about 0.25005 to about 0.75075 mm, 0.25 to about 0.5010 to about 0.050 mm, about 0.015 to about 0.025 mm, about 0.020 to about 0.060 mm, about 0.020 to about 0.040 mm, about 0.040 to about 0.100 mm, about 0.040 to about 0.060 mm, about 0.060 to about 0.150 mm, or about 0.060 to about 0.125 mm. The mean particle size may be bi-modal to include any combination of mean particle sizes as previously described. These granules may exhibit a mean granule size of about 0.050 mm to about 5 mm, about 0.100 to about 1.500 mm, about 0.125 to 1.000 mm, 0.125 to 0.500 mm, about 0.125 to 0.250 mm, about 0.250 to 0.750 mm, about 0.250 to 0.500 mm, about 0.500 to 1.00 mm, about 0.500 to 0.750 mm. The mean granule size may be multi-modal to include any combination of mean granule sizes as previously described. In some embodiments, varying sizes of said powders or granules may be used in the adhesive composition.

In some embodiments, certain additives may be provided as fibers. In some embodiments, the fibers may exhibit a mean fiber diameter of about 0.010 mm to about 2 mm, about 0.010 mm to about 0.50 mm, or about 0.025 mm to about 0.075 mm. These fibers may exhibit a mean fiber length of about 0.025 mm to about 50.0 mm, about 0.50 mm to 10 mm, or about 1.00 mm to about 3.50 mm. The mean fiber diameter or length may be multi-modal to include any combination of mean fiber diameter or length as previously described.

The term adhesion as used herein may include reference to the molecular force of attraction in the area of contact between like or unlike bodies that acts to hold them together. In some embodiments, adhesion comprises molecular and atomic level attraction and does not include a macro level of interlocking structures. Exemplary molecular forces include covalent bonding, ionic bonding (e.g., cationic and anionic interactions), chelation, van der Waals interactions, dipole forces, and other interactions between molecular and submolecular elements. In some embodiments, an adhesive process provides resistance to displacement of the interacting macro elements. These microelements might include the set composition in contact with other surfaces, e.g., bone, teeth, or other materials (e.g., metallic structures, ceramic structures, polymeric structures, or glass structures).

The term adhesively as used herein may include producing a molecular bond in the area of contact between the applied material and the surface to which it is applied. In some embodiments, application of the composition comprises adhesive application.

The term luting as used herein may include fastening or cementing of objects in a fixed special relationship by means of interlocking mechanically with surface irregularities and also providing frictional resistance to displacement. Luting may also include fastening or cementing objects in a fixed spacial relationship by means of interlocking mechanically with surface irregularities and also providing frictional resistance to displacement. Generally, luting agents may be applied as a flowing material into a void between non-convex solid surfaces, one generally enclosing the other, and hardening as a solid which fills the space and rigidly interlocks the surfaces of the objects and resists their relative displacement.

In some embodiments, the term structure as used herein denotes a solid object. A solid object may comprise an artificial device or a biological tissue, such as a synthetic graft material (e.g., bone void filler, bone cement, hardened adhesive composition), an implant device (e.g., orthopedic, dental), transdermal abutment device, or prosthetic device. Implant devices may take on several forms including a rod, pin, post, stem, screw, anchor, plate, cage, or other implantable device intended to attach to bone (e.g., cochlear implant, maxillofacial implant). Prosthetic devices might comprise a dental crown, limb replacement device, joint replacement device. Transdermal or transmucosal abutment devices might comprise a dental abutment, limb prosthetic attachment device, or other devices intended to attach an implant to a prosthetic device. Biological tissues might comprise a tissue graft (e.g., autograft, allograft, or xenograft), tendon, ligament, bone, bone fragment, or bone block.

The artificial devices might substantially comprise a bioresorbable surface for adhesion with the adhesive composition. In some embodiments, the bioresorbable component comprises inorganic materials (e.g., calcium phosphates, calcium carbonates, calcium sulfates, calcium oxides, bioglass, or mixtures thereof). In other embodiments, the bioresorbable component comprises polymeric materials (e.g., poly(lactide), poly(glycolide), poly(ε-caprolactone), poly(teramethylglycolic-acid), poly(dioxanone), poly(hydroxybutyrate), poly(hydroxyvalerate), poly(lactide-co-glycolide), poly(glycolide-co-trimethylene-carbonate), poly(glycolide-co-caprolactone), poly(glycolide-co-dioxanone-co-trimethylene-carbonate), poly(tetramethylglycolic-acid-co-dioxanone-co-trimethylene-carbonate), poly(glycolide-co-caprolactone-co-lactide-co-trimethylene-carbonate), poly(hydroxybutyrate-co-hydroxyvalerate), polyamines, polyamides, polyimidazoles, poly(vinyl-pyrrolidone), chitosan, hyaluronic acid, gelatin, or a copolymer, derivative, or mixture thereof). In some embodiments the permanent surface is treated to promote a hydrophilic surface.

The artificial devices might substantially comprise a permanent surface for adhesion with the adhesive composition. In some embodiments, the permanent surface comprises silk, nylon, polyamides, glass, carbon, aromatic (e.g., polyphenylene vinylene) and conjugated (e.g., polyacetylene) polymers, intrinsically conductive polymers (e.g., polyaniline, polypyrrole, polythiophene), metals (e.g., calcium, silicon, copper, silver, gold, zinc, iron, titanium, aluminum, cobalt, chromium, tantalum, molybdenum), metallic alloys (e.g., bronze, brass, steel (e.g., stainless steel), cobalt-chromium), poly(ether ketone), poly(ethylene), poly(urethane), poly(methyl methacrylate), poly(carbonate), or poly(acrylic acid) polymers or a copolymer, derivative, or mixture thereof. In some embodiments the permanent surface is treated to promote a hydrophilic surface.

Uses of the Adhesive Compositions

The adhesive compositions may be useful in a wide variety of applications. In some embodiments, the adhesive compositions may be used to adhere a structure to a surface (e.g., a bone or another structure, e.g., as shown in FIGS. 1-20). In some embodiments, the structure comprises an implant, anchor, graft, device, biological tissue, or another bone or bone fragment. In some embodiments, the surface is the endosseous surface or the subperiosteal surface of the bone. In some embodiments, the adhesion of said structure is temporary, such that said structure is removed after a period of time (e.g., greater than about 1 hour, about 2 hours, about 12 hours, about 24 hours, about 1 week, about 1 month, about 6 months, about 1 year, about 5 years). In other embodiments, the adhesion of said structure is permanent or intended to be permanent or until the material is resorbed and replaced with bone.

Figure 2:
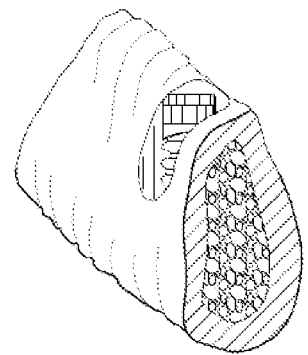
FIG. 2 is a drawing of a dental implant placed into an alveolus with insufficient bone contact to provide primary stability.
Figure 3:
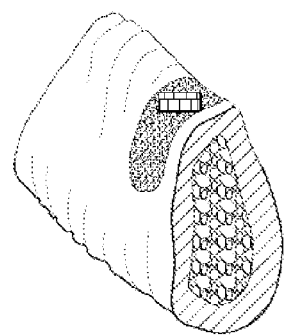
FIG. 3 is a drawing showing an alveolus filled with an exemplary adhesive composition that surrounds the dental implant, resulting in primary stability of the implant after hardening of the composition. In this depiction, the exemplary adhesive composition further serves as a seal to prevent fibrous tissue ingrowth from overlying gingiva and also to prevent microbial ingress from forming an oral cavity into bone tissues.
Figure 17:
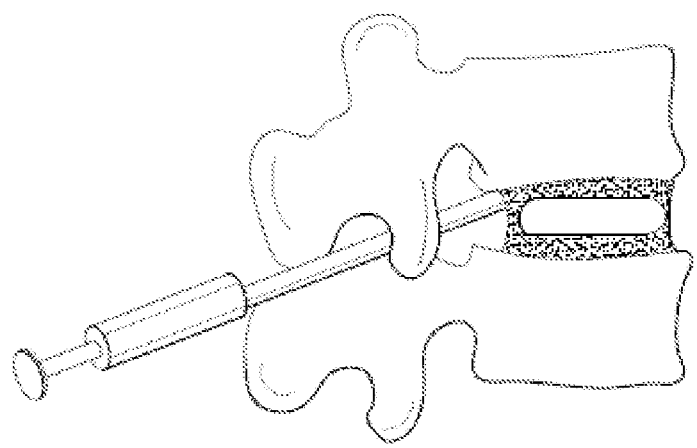
FIG. 17 is a representation of an interbody fixation of adjacent spinal vertebral bodies in which application of an exemplary adhesive composition provides primary fixation of the interbody cage device upon hardening of the composition.

In other embodiments, the adhesive compositions may be used to fill a gap, hole, or void in a surface either before (e.g., a bone or other structure, e.g., as shown in FIGS. 4-15) or after placement of a structure into or onto a surface (e.g., implant, anchor, graft, device, biological tissue, or another bone or bone fragment, e.g., as shown in FIGS. 1-3). It is envisioned that this particular application may be useful when the core diameter of the gap, hole, or void is larger than the size of the structure, for instance, in the placement of a dental implant into the alveolar ridge (e.g., as shown in FIGS. 1-3). In this instance, the adhesive composition may impart additional strength, fixation, stability, durability, or other advantageous property to the attached structure at the attachment site. In other embodiments, the adhesive composition may impart fixative strength to the attached structure at the attachment site (e.g., as shown in FIG. 17). In some embodiments, the adhesive compositions may support new bone growth at the attachment site, e.g., by increasing or stimulating the bone resorption, deposition, or the remodeling rate. In additional embodiments, the adhesive compositions may be used to fill gaps created in or at the attachment site to create a seal (e.g., as shown in FIGS. 1-3 and FIG. 22), prevent leakage, or prevent microbial growth (e.g., an infection), or prevent fibrous tissue ingress. In some embodiments, the adhesive compositions may be used to prevent microbial ingress, e.g., to prevent an infection, e.g., to prevent fibrous tissue ingress (e.g., as shown in FIGS. 1-3 and FIG. 22).

In some embodiments, the adhesive compositions are used during a medical procedure. In some embodiments, the adhesive compositions are used during a surgical or dental procedure. In some embodiments, said medical procedure comprises a surgery (e.g., dental surgery, sinus surgery, facial surgery, or other surgery to the skeletal region). In other embodiments, the medical procedure comprises a spinal fusion, prosthetic limb attachment, skeletal cosmetic augmentation, or other surgery to the musculoskeletal system. The surgical procedures may be through open tissue procedures to expose or gain access to the application site. Likewise, the surgical procedures may be through small incisions or through minimally invasive approaches in order to minimize tissue damage (e.g., with needle access to an application site and to inject an exemplary composition during spinal fusion procedures as shown in FIGS. 16-20). Such surgical procedures could be performed in sterile operating rooms or in non-sterile settings such as at a clinic, office setting, or at a remote site outside a hospital setting (e.g., injury site, battlefield, ocean, ambulance).

In some embodiments, the compositions may be used in a dental application (e.g., ridge preservation graft following tooth extraction, filling of a cavity or defect resulting from tooth decay, fracture, attrition, abrasion, erosion, abfraction, placement of a dental implant or device, osteoperiosteal graft, endodontic reconstruction, or others). In some embodiments, the compositions are used as an onlay graft to increase bone volume (e.g., as shown in FIGS. 4-16 and FIG. 18). In some embodiments, the compositions are for the cutting of a tooth. In other embodiments, the adhesive compositions may be used in ossicular chain reconstruction or to adhere a structure to the inner ear or middle ear, e.g., a hearing aid. In other embodiments, the adhesive compositions may be used to provide contour in a surgical application, e.g., for facial bone augmentation applications. In some embodiments, the adhesive compositions may be used in a cosmetic application.

In other embodiments, compositions are placed by injection into an extraction socket and allowed to become solid. The solid material is allowed to remain undisturbed until the composition hardens, cures, or resorption of the material proceeds, resulting in increased bone volume through alveolar fill graft and ridge preservation.

In other embodiments, the adhesive compositions are placed or injected into a bone void resulting from the removal of a bone cyst, or granuloma, or similar bone defect crestal, central, or lateral to the ridge (e.g., bone), and allowed to become solid. The solid material is allowed to remain undisturbed until the resorption of the material proceeds, resulting in increased bone strength and restoration of the bone contour.

In other embodiments, the adhesive compositions are placed or injected into a bone void partially or totally surrounding the superficial aspect of a structure (e.g., an implant) as it emerges from the bone, thereby providing continuous contour to the surface of the bone, augments the stability of the structure (e.g., implant) in the bone if needed, and excludes fibrous tissue cells from the void. In some embodiments, the adhesive are placed or injected into a bone void partially or totally surrounding the superficial aspect of a structure to seal a gap to exclude fibrous tissue or prevent microbial ingress (e.g., prevent an infection, e.g., as shown in FIGS. 1-3 and FIG. 22). In some embodiments, this might be performed during an initial visit after an implant is placed. In other embodiments, this might be performed during a rescue procedure of an implant.

In other embodiments, the adhesive compositions are placed or injected into a prepared extraction socket, or a similar bone void, and a structure (e.g., an implant) is placed into this preparation in desired relationship to the surroundings before the composition becomes solid. Once the composition becomes solid, the structure (e.g., an implant) possesses primary stability, in some embodiments may mean that the implant body is clinically immobile relative the bone host site in lateral and axial load, and in torsional load of at least 10 N/cm of clockwise seating rotation. In some embodiments, primary stability may mean that the implant body is clinically immobile relative the bone host site when using a Ostell meter that uses Resonance Frequency Analysis with an ISQ value measured, wherein the ISQ scale is normalized from 0-100, wherein the higher the ISQ the more stable the implant, and/or wherein an ISQ value >50 has been clinically accepted to indicate the implant is sufficiently stable to allow for loading. In other embodiments, primary stability refers to the relative immobility of the adhered surfaces that persist when the adhesive bond is subjected to load-bearing stress of at least 250 kPa.

The placement of endosseous structures might be performed through open procedures involving partial or full thickness flap reflection or performed through flapless procedures with minimal periosteal reflection (e.g., punch access, laser, electro cautery, etc.).

The placement of the adhesive composition in contact with bone might be performed through open procedures involving partial or full thickness flap reflection or performed through flapless procedures with minimal soft tissue incision or interruption (e.g., injection through cannula or needle following a tunneling approach to gain access).

The adhesive composition might be applied to the surface of a structure in its fluid or semi-solid state by means of an injection delivery device or by application using an instrument such as a spatula. The viscosity of the adhesive composition when in its fluid state might be as low as about 100 cP to about 10,000 cP and when it reaches its semi-solid state from about 10,000 cP to about 250,000 cP. The viscosity and cohesion properties of the adhesive composition will facilitate the ability to squeeze the material through a needle or cannula as small as 18 gauge when the viscosity is in the low range of its fluid state. With viscosities in the semi-solid state, the shape and amount of material can be altered through spreading or removal techniques without substantially effecting the strength of the set material. In some embodiments, the working time of the adhesive composition is when the viscosity is between about 100 cP to about 250,000 cP.

The adhesive composition might be applied to a surface of a host structure in its fluid or semi-solid state and remain in these states during the subsequent placement of an another structure in contact with the adhesive composition before the adhesive composition hardens to a solid, whereupon the structure possesses primary stability.

The adhesion of structures to a host structure might be performed into a bed, mantle, or layer of the adhesive composition that surrounds, contacts, or embeds the structure while the adhesive composition is in a fluid or semi-solid state prior to hardening, whereupon the structure possesses primary stability (e.g., as shown in FIGS. 1-3, 13-15, and 21-22). To do so, the host site for the structure may first require a preparation prior to application of the adhesive composition. The adhesive composition may be applied to the host site which may have a convex or concave or a combination of concave and convex surfaces. The adhesive composition may have sufficient cohesion and adhesion to the host site while in its fluid or semi-solid state to resist displacement from gravity, hydrostatic pressure, or fluid flow acting upon it. The structure may be placed into or onto the adhesive composition while in its fluid or semi-solid state in a desired location relative to the surroundings before the adhesive composition hardens, whereupon the structure possesses primary stability. Alternatively, the structure might be placed into or onto the host site in a desired location relative to the surroundings and subsequent to this an adhesive composition might be injected around or through a cannulation or orifice feature of the implant device that which communicates to the surface of the host site before the adhesive composition hardens, whereupon the structure possesses primary stability. Alternatively, the structure might be first coated on some or all of its surfaces with an adhesive composition and subsequently placed onto or into the host site before the fluid adhesive composition hardens, whereupon the structure possesses primary stability.

Figure 4:
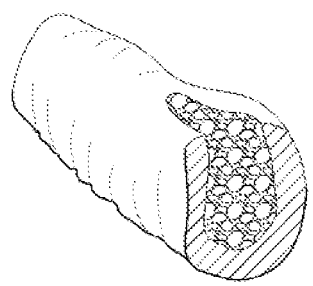
FIG. 4 is a drawing showing a mandibular alveolar ridge which lacks height to adequately retain a dental implant. The state of the alveolar ridge in its clinically presenting state or before the site has been prepared (by, e.g., milling, drilling, reaming) is shown, ready to accept adhesive composition.
Figure 5:
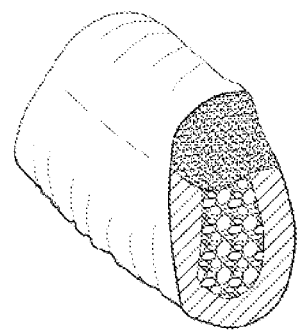
FIG. 5 is a drawing of an onlay graft in which an exemplary adhesive composition has been applied to provide vertical ridge augmentation and to add sufficient ridge volume.
Figure 6:
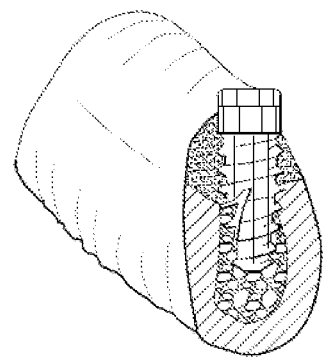
FIG. 6 is a drawing of a dental implant placed into an exemplary adhesive composition and alveolar ridge after vertical ridge augmentation. In this example, implant primary stability is attained after the composition hardens. The dental implant may be placed into the composition alone or into a composite of the composition and bone, either during the pliable working time of the composition or at some point after hardening, at which point it may be milled, drilled, or reamed to accept the implant.
Figure 7:
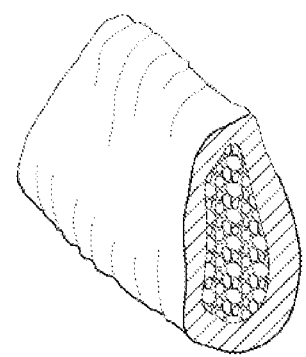
FIG. 7 is a drawing showing a deficient mandibular alveolar ridge (e.g., marginally insufficient in width) that lacks sufficient bone volume for predictable maintenance of the bone after dental implant placement. The state of the alveolar ridge in its clinically presenting state or before the site has been prepared (by, e.g., milling, drilling, reaming) is shown, ready to accept adhesive composition.
Figure 8:
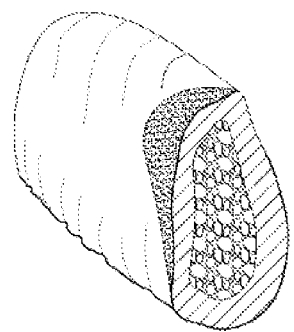
FIG. 8 is a drawing of a lateral onlay graft in which an exemplary adhesive composition has been applied to provide lateral ridge augmentation and to produce sufficient ridge volume.
Figure 9:
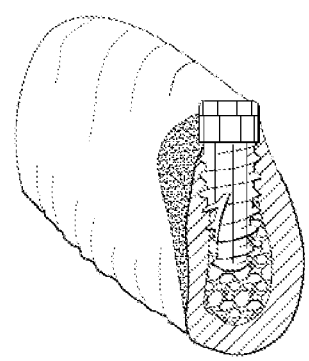
FIG. 9 is a drawing of a dental implant placed into an exemplary adhesive composition and alveolar ridge after a lateral ridge augmentation. In this example, implant primary stability is attained after the composition hardens. The dental implant either placed into the composition alone or into a composite of composition and bone, either during the pliable working time of the composition or at some point after hardening, at which point it may be milled, drilled, or reamed to accept the implant.
Figure 10:
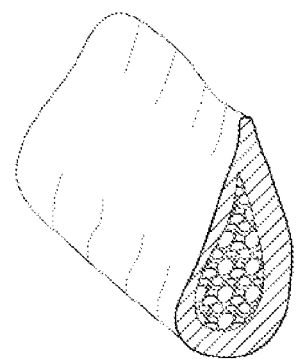
FIG. 10 is a drawing showing a mandibular alveolar ridge (e.g., a knife-edge ridge) that severely lacks volume for dental implant placement because of insufficient width. The state of the alveolar ridge in its clinically presenting state or before the site has been prepared (by, e.g., milling, drilling, reaming) is shown, ready to accept adhesive composition.
Figure 11:
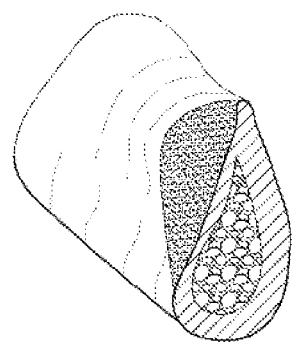
FIG. 11 is a drawing of a lateral onlay graft in which an exemplary adhesive composition has been applied to provide to produce sufficient ridge volume.
Figure 12:
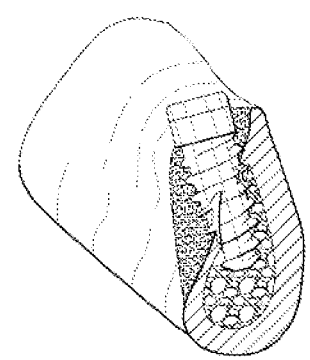
FIG. 12 is a drawing of a dental implant placed into a composite of an exemplary adhesive composition and the alveolar ridge bone after a lateral ridge augmentation. In this example, implant primary stability is attained after the adhesive composition hardens. The dental implant is place either into the composition alone or into a composite of the composition and bone, either during the pliable working time of the composition or at some point after hardening, at which point it may be milled, drilled, or reamed to accept the implant.
Figure 13:
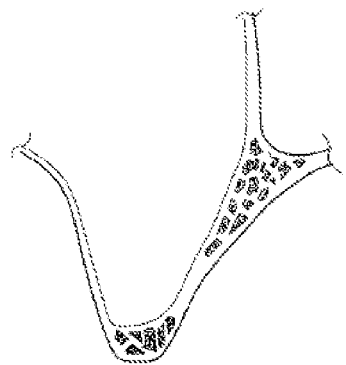
FIG. 13 is a cross-sectional presentation of a maxillary alveolar ridge that lacks volume for dental implant placement.

In other embodiments, the alveolar ridge is augmented with an adhesive composition to create an increase in ridge bone volume concurrent with placement of a dental implant per the following technique. First, the alveolar ridge may require an initial step to prepare the bone surface, which may include drilling or reaming the available bone to a desired state (e.g., as shown in FIGS. 4, 7, and 10). Next, an adhesive composition is adhesively applied to the alveolar ridge (e.g., as shown in FIGS. 5, 8, and 11). A dental implant is placed into the adhesive composition in a desired location relative to the surroundings before the adhesive composition hardens to the solid state, whereupon the implant possesses primary stability. The implant may partially or may not engage bone in the alveolar ridge that was previously prepared (e.g., as shown in FIGS. 6, 9, and 12). Further, the healing, temporary, or definitive abutment, and a temporary or definitive crown may be placed on the dental implant either during the same procedure at a subsequent step or at a subsequent procedure after a sufficient time interval has elapsed for soft tissue and bone healing to occur. The interval might be equal to or less than twenty-four hours, twenty-four hours to one week, one week to two weeks, two weeks to one month, one month to three months, three months to six months, six months to one year, or more than one year. The crown, implant, abutment, material and surrounding bone are all subjected and able to maintain primary stability when subjected to patient loading (e.g., chewing forces).

The adhesion of structures might be performed into the hardened adhesive composition following an interval. The interval might be equal to or less than an hour, more than an hour but less than eight, eight hours to twenty-four, twenty-four hours to one week, one week to two weeks, two weeks to one month, one month to three months, three months to six months, six months to one year, or more than one year. To do so, a preparation may be milled (e.g., drilled) into the substrate composed of the solidified adhesive composition and the surrounding bone. The structure might be placed directly into the preparation in a desired location relative to the surroundings, whereupon the structure possesses primary stability (e.g., as shown in FIGS. 3, 6, 9, 12, and 15). Alternatively, the preparation might be first partially or totally filled with an adhesive composition and the structure might be subsequently placed into the preparation in a desired location relative to the surroundings while the adhesive composition is in its fluid or semi-solid state and whereby the structure displaces the adhesive composition during placement before the fluid adhesive composition hardens, whereupon the structure possesses primary stability (e.g., as shown in FIGS. 3, 6, 9, 12, and 15). Alternatively, the structure might be placed into the preparation in a desired location relative to the surroundings and subsequent to this an adhesive composition might be injected through a cannulation or orifice feature of the implant device that which communicates to the surface of the preparation before the adhesive composition hardens, whereupon the structure possesses primary stability. Alternatively, the structure might be first coated on some or all of its surfaces with an adhesive composition and subsequently placed into the preparation before the fluid adhesive composition hardens, whereupon the structure possesses primary stability.

In other embodiments, the alveolar ridge is augmented with an adhesive composition to create an increase in ridge volume (width or height) concurrent with placement of a dental implant per the following technique. In some embodiments, the alveolar ridge may require an initial step to prepare the bone surface, which may include drilling or reaming the available bone to a desired state (e.g., as shown in FIGS. 4, 7, and 10). In some embodiments, the adhesive compositions may then be placed or injected into a prepared extraction socket and is allowed to become solid. A preparation can then be milled (e.g., drilled) into the substrate composed of the solidified material and the surrounding bone. Then compositions of either similar or different compositions in its fluid state (i.e., working state) are placed into the preparation and/or applied onto the surface of the implant (e.g., dental implant). The implant is placed into the preparation in a desired location relative to the surroundings before the fluid material hardens to the solidified cement state, whereupon the implant possesses primary stability (e.g., as shown in FIGS. 6, 9, and 12). Further, the healing, temporary, or definitive abutment, and perhaps a temporary or definitive crown may be placed on the dental implant either during the same procedure at a subsequent time interval or at a subsequent procedure after sufficient time has elapsed for soft tissue and bone healing to occur to a desired state. The interval might be equal to or less than twenty-four hours, twenty-four hours to one week, one week to two weeks, two weeks to one month, one month to three months, three months to six months, six months to one year, or more than one year. In some embodiments, the crown, implant, abutment, material and surrounding bone are all subjected and able to maintain primary fixation when subjected to immediate patient loading (e.g., chewing forces). In other embodiments, the crown, implant, abutment, material and surrounding bone are all subjected and able to maintain primary stability when subjected to patient loading (e.g., chewing forces).

In other embodiments, a full thickness incision (e.g., a distant full thickness incision) followed by a tunneling subperiosteal dissection and a subperiosteal placement or injection of the adhesive compositions in contact with bone are used to produce augmentation of the bone volume in the area. This might be a widening of the alveolar ridge where a dental implant placement is desired, but where the width of the residual ridge of bone is marginally insufficient for implant placement. The ridge so augmented is sufficiently broad for an osteotomy to be performed within the original bone volume, either at the time of the original procedure or after a delay of days, weeks, or months, and for the adhesive compositions placed, in the hardened state or as altered by the host, to provide resistance to lateral movement of the rotary cutting instrument during bone preparation and to the implant on placement into its planned relationship to the surrounding host bed.

In other embodiments, with an alveolar residual ridge deficient in width thus limiting implant placement options, a full thickness incision and flap reflection are made, followed by application of an adhesive composition in contact with bone, are used to produce augmentation of the bone volume in the area (e.g., as shown in FIG. 11). This might be a widening of the alveolar ridge where a dental implant placement is desired, but where the width of the residual ridge of bone is initially marginally insufficient for implant placement. The ridge so augmented is as a result then sufficiently broad for an osteotomy to be performed within the original bone volume, either at the time of the original procedure or after a delay of days, weeks, or months, and for the adhesive compositions placed, in the hardened state or as altered by the host, to provide resistance to lateral movement of the rotary cutting instrument during bone preparation and to the implant on placement into its planned relationship to the surrounding host bed.

In other embodiments, a full thickness incision (e.g., a distant full thickness incision) followed by a tunneling subperiosteal dissection and a subperiosteal application of an adhesive composition in contact with bone are used to produce augmentation of the bone volume in the area (e.g., as shown in FIGS. 8 and 11). This might be increasing the height of the alveolar ridge where a dental implant placement is desired, but where the height of the residual ridge of bone is initially marginally insufficient for implant placement (e.g., as shown in FIG. 5). The augmented ridge composed of the original bone and the adhesive composition is as a result then sufficiently high for an osteotomy to be performed, either immediately or after a delay of hours, days, weeks, or months, and for the adhesive compositions placed, in the hardened state or as altered by the host, to provide resistance to lateral movement of the rotary cutting instrument during bone preparation and to the implant on placement into its planned relationship to the surrounding host bed.

In other embodiments, with an alveolar residual ridge deficient in height thus limiting implant placement options, a full thickness incision and flap reflection are made, followed by application of an adhesive composition in contact with bone, are used to produce augmentation of the bone volume in the area (e.g., as shown in FIG. 5). This might be to increase the total height of available volume for dental implant placement. The volume so augmented is as a result then sufficiently tall for an implant recipient site to be milled into it, either immediately or after a delay of hours, days, weeks, or months, and for an adhesive compositions placed, in the hardened state or as altered by the host, to provide resistance to lateral movement of the rotary cutting instrument during bone preparation and to the implant on placement into its planned relationship to the surrounding host bed.

In other embodiments, the ridge so augmented is sufficiently broad for an osteotomy to be performed within the volume of the wider solid composed of the bony ridge and the additional adherent material, in the hardened state or as altered by the host. In some embodiments, the implant host bed is a combination of the preexisting bone, the compositions, or the compositions as altered by the host, throughout the length of the implant. In other embodiments, the ridge so augmented is sufficiently high for an osteotomy to be performed within the volume of the higher solid composed of the bony ridge and the additional adherent material, in the hardened state or as altered by the host. Alternatively, the implant placement is delayed until the composition is partially or totally resorbed and replaced by bone. In this embodiment the most superficial layer of the implant host site bed is the composition or the composition as altered by the host, and the deepest part of the bed is the bone volume present before the composition was placed.

Figure 14:
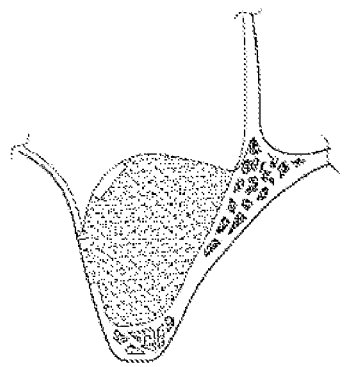
FIG. 14 is a cross-sectional presentation of the maxillary alveolar ridge from FIG. 13 after an exemplary adhesive composition is applied in a sinus lift procedure to augment the ridge height, thereby gaining sufficient volume for implant placement.
Figure 15:
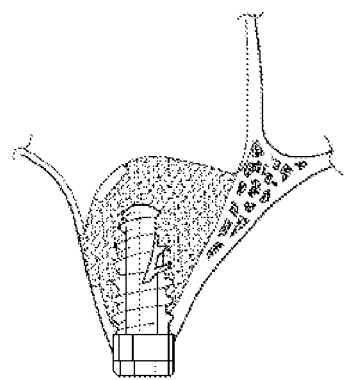
FIG. 15 is a cross-sectional presentation of the maxillary alveolar ridge showing a dental implant placed into a composite of an exemplary adhesive composition and the alveolar ridge bone after a sinus lift procedure. In this example, implant primary stability is attained after the composition hardens. The dental implant is place either into the composition alone or into a composite of the composition and bone, either during the pliable working time of the composition or at some point after hardening, at which point it may be milled, drilled, or reamed to accept the implant.

In some embodiments, a subperiosteal injection or placement of the adhesive compositions in contact with bone is performed between the mucoperiosteum of a facial sinus or another air space (e.g., the nasal airway, e.g., as shown in FIG. 14). In some embodiments, the facial sinus comprises the paranasal sinus, e.g., the maxillary sinus. This might be an augmentation in height of the bone volume where a dental implant placement is desired, but where the height of the residual bone between the oral cavity and the sinus air space is insufficient for implant placement. The bone so augmented is sufficiently high for an osteotomy to be performed within the volume of the higher solid comprised of the bone and the additional adherent material, in the hardened state or as altered by the host. Alternatively, the implant placement is delayed until the composition is resorbed and replaced by bone, in part or totally. In this embodiment the deepest layer of the implant host site bed is the composition or the composition as altered by the host, and the most superficial part of the bed is the bone volume present before the material was placed.

In some embodiments, the compositions might be adhesively applied to bony walls of a gap or a discontinuity between bone surfaces which are indicated for closure because the gap or the discontinuity of bone causes a disability, a dysfunction, or is otherwise undesirable. In some embodiments, the gap or the discontinuity of bone is undesirable because of loss of load-bearing function. These may include a gap or discontinuity which is congenital (e.g., cleft palate), a result of trauma (e.g., bone fracture), result of inappropriate healing (e.g., fibrous union), a result of a resection of bone (e.g., neoplasm, necrosis, or infection), or a result of procedure involving cutting or segmentation of bone in order to change its size, shape, or contour (e.g., orthognathic procedure, or correction of deformed long bones resulting from congenital, metabolic or dietary problems). The composition might be used in conjunction with fixation devices, such as microplates, bone pins and screws, or with shape and volume preserving devices, such as titanium meshes or cages, which relate the bone fragments across the gap or exclude other tissues, or it may be used alone or in combination of several formulations of the composition including those that release substances intended to affect surrounding tissues and environment. In this embodiment, the composition performs a bridging function with respect to existing elements of the skeleton, providing continuity of contour, a mechanical connection, and preventing other tissues from proliferating while bone tissue replaces the solidified material. In some embodiments, the mechanical connection is a load-bearing connection.

In some embodiments, the disclosure features a method of reinforcing a bone (e.g., osteoporotic, osteopetrotic, or affected by osteogenesis imperfecta) at risk of fracture, the method comprising: a) preparation of an adhesive composition comprising a multivalent metal salt and a small organic phosphate compound in an aqueous solution or suspension; b) adhesive application of the composition to the desired region of the bone and also adhesively applied to one, or plurality of rigid, or semi-rigid devices (e.g., plates, rods, strips, bands) comprised of metal or other biocompatible material; c) applying the device of b) adhesively attached to the bone to the desired region of bone; and d) allowing the composition to remain undisturbed until the composition is hardened, cured, or resorbed and replaced by bone. In some embodiments, the bone is osteoporotic, osteopenic, osteopetrotic, or affected by osteogenesis imperfecta.

In some embodiments, the disclosure features a method of repairing a fractured bone (e.g., osteoporotic femur) fracture, the method comprising: a) preparation of an adhesive composition comprising a multivalent metal salt and a small organic phosphate compound in an aqueous solution or suspension; b) adhesive application of the composition to the desired region of the bone and also adhesively applied to one, or plurality of rigid, or semi-rigid devices (e.g., plates, rods) comprised of metal or other biocompatible material; c) applying the device of b) adhesively attached to the bone to the desired region of bone; and d) allowing the composition to remain undisturbed until the composition is hardened, cured, or resorbed and replaced by bone.

Figure 18:
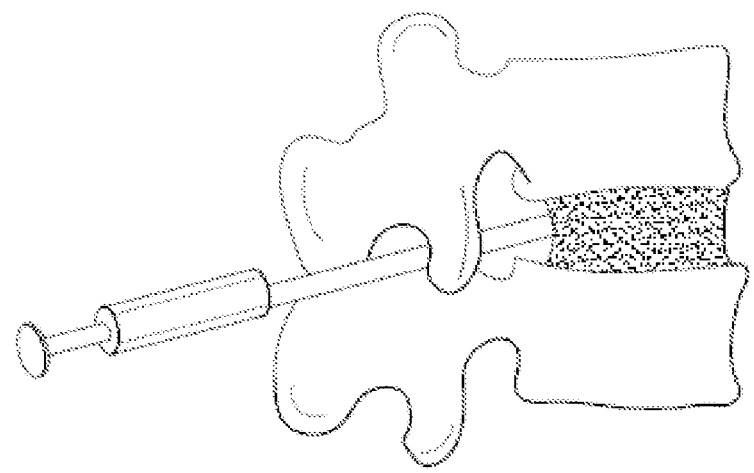
FIG. 18 is a representation of an interbody fixation of adjacent spinal vertebral bodies in which application of an exemplary adhesive composition bridges the gap to provide primary fixation after the composition hardens.
Figure 21:
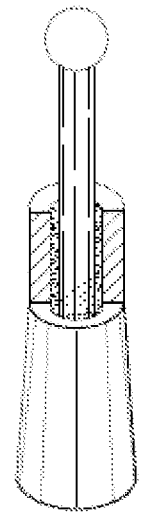
FIG. 21 is a schematic representation of the attachment of an element of a prosthetic limb to an amputation bone stump with an exemplary adhesive composition. Part of the structure shown is inserted into the medullary space of the long bone (e.g. femur) and stabilized for load bearing support, and the adhesive composition is applied to fill the space between the surfaces of the device and the adjacent surfaces of the supporting bone, resulting in primary fixation of the device upon hardening of the composition. Note that the surface of the bone is not drawn to show the details of intramedullary space.

In some embodiments, the composition is adhesively applied to a gap, discontinuity, or loss of volume in bone (e.g., femur, e.g., as shown in FIGS. 21-22; alveolar ridge, e.g., as shown in FIGS. 4, 7, 10, and 13), or to a gap, discontinuity, or loss of volume between bones (e.g., spinal processes, vertebral bodies as shown in FIGS. 17 and 18). In some embodiments, the gap or the discontinuity causes a disability, a dysfunction, or is otherwise undesirable. The gap or discontinuity may be congenital (e.g., cleft palate), a result of trauma (e.g., bone fracture), a result of a resection of bone (e.g., neoplasm, necrosis, or infection), or a result of procedure involving cutting or segmentation of bone in order to change its size, shape, or contour (e.g., orthognathic procedure, correction of deformed long bones resulting from congenital, metabolic or dietary problems). In other embodiments, the gap or discontinuity may be a result of a resection of soft tissue (e.g., removal of cartilage or discectomy, e.g., as shown in FIGS. 17 and 18). In some embodiments, the composition is used alone. In other embodiments, the composition is used in conjunction with rigid devices, such as microplates, plates and objects of other shapes, composed of metal or other solid material, shape and volume preserving devices, such as titanium meshes, which relate the bone fragments across the gap or exclude other tissues, or it may be used alone or in combination of several formulations of the composition including those that release substances intended to affect surrounding tissues and environment. In some embodiments, the composition may be used in conjunction with interbody devices (e.g., cages, e.g., as shown in FIG. 17). In this embodiment, the composition performs a bridging function with respect to existing elements of the skeleton, providing continuity of contour, a mechanical connection, and preventing other tissues from proliferating while bone tissue replaces the solidified material.

Figure 16:
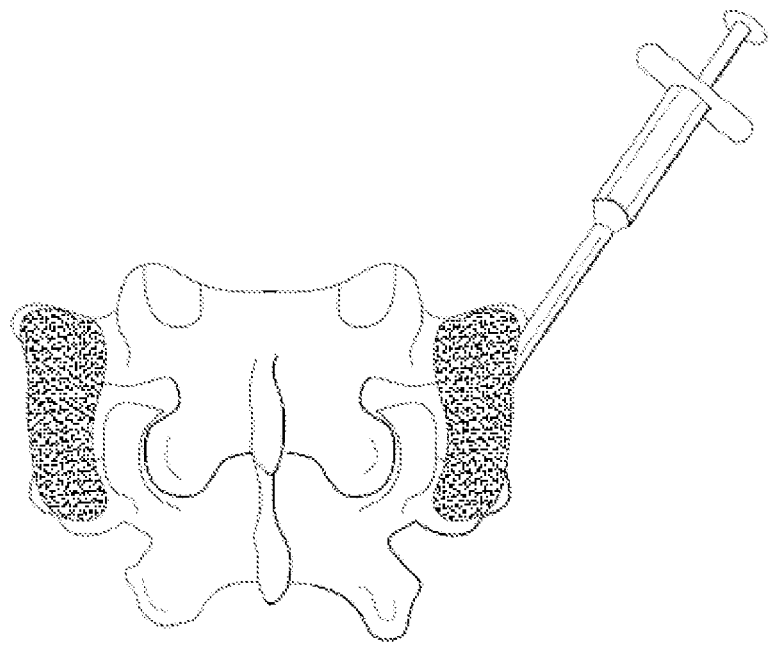
FIG. 16 is a representation of a posterolateral fixation of adjacent spinal vertebral bodies in which application of an exemplary adhesive composition bridges the gap between transverse processes to provide primary fixation after the composition hardens. Here, the bilateral fixation is shown.
Figure 19:
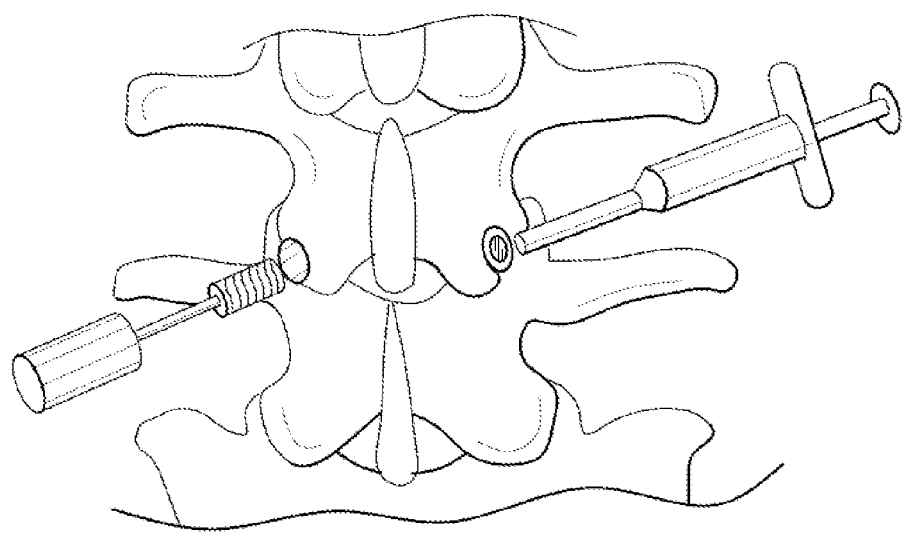
FIG. 19 is a representation of a facet joint preparation to create a drilled hole between adjacent spinal vertebral bodies (shown on the left side), with subsequent application of a facet joint pin device into the hole and its stabilization with an exemplary adhesive composition to provide primary fixation of facet joint (shown on the right side) after the composition hardens.
Figure 20:
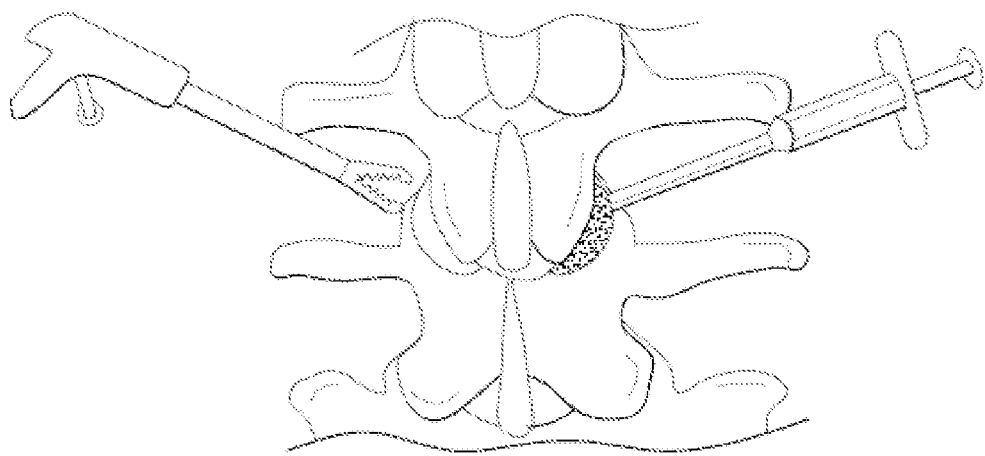
FIG. 20 is a drawing of a facet joint preparation with an exemplary tool (e.g., rongeurs) used to remove articular cartilage and decorticate surfaces of the facet joint between adjacent spinal vertebral bodies (shown on the left side) with subsequent application of an exemplary adhesive composition to provide primary fixation of a facet joint (shown on the right side) after the composition hardens.

In some embodiments, the adhesive composition is applied between articulating bone surfaces (e.g., facet joints, e.g., as shown in FIG. 19) or is applied to adjacent bone surfaces to bridge a gap space (e.g., between vertebral bodies. e.g., as shown in FIG. 18; between transverse processes, e.g., as shown in FIG. 16; or between spinous processes) to prevent relative displacement of the bone surfaces (e.g. spinal fusion procedures) and to provide load bearing support with or without supportive implants devices (e.g., screws, plates, interbody cages, e.g., as shown in FIG. 17). These applications might be made singly or to provide multipoint fixation when applied in several of the above or other, loci.

In some embodiments, the adhesive compositions are adhesively placed or injected in contact with bone, into a space adjacent to or a gap between volumes of bone, where it is desired to affix implants or other devices (e.g., as shown in FIGS. 21-22). The device might be placed, embedded, or otherwise affixed to the composition and the host bed at a time prior to the composition adopting the cement state, during the setting process, after the composition is solid, or after the composition is partially or totally replaced with bone tissue.

In some embodiments, the adhesive compositions are placed or injected into a bone defect associated with a root of a tooth (e.g., a periodontal defect) and allowed to solidify. In some embodiments, the bone defect associated with a root of a tooth is a periodontal or periapical defect. The compositions may then be replaced by bone providing increased mechanical stability to the tooth and also barring environmental microbiota from access to the root surface and the interior of the alveolar socket.

In other embodiments, the adhesive compositions are placed or injected into a bone defect associated with a dental implant (e.g., a periimplantitis defect) and allowed to solidify. The compositions may then be replaced by bone providing increased mechanical stability to the implant and also barring environmental microbiota from access to the implant surface and the surrounding bone.

In some embodiments, the adhesive compositions might have adhesive properties toward soft tissues. A layer of the composition might be applied as an adhesive to immobilize soft tissue flaps, fragments, or zones. The attachment of the composition to the soft tissues might be durable enough and strong enough to close wounds. The attachment of the composition might provide a barrier to flow of fluids from one side of the attachment to another side. The attachment of the composition might provide a barrier to movement of microbes from one side of the attachment to another side. The surface of the composition might be a barrier to the movement of soft tissue cells (e.g., fibroblasts) into the interior of the set material. The surface of the composition might be a barrier to the movements of microbes into the interior of the set composition.

In some embodiments, the adhesive compositions might be injected or otherwise placed at the percutaneous or permucosal site of an implant or device placement to seal the site from incursion of fluids, materials, and microbiota or their products deeper into the wound. This application might be contemporaneous with the initial placement of the implant or another later procedure involving the implant. The implant might be a dental implant, a maxillofacial prosthesis fixation implant or any other implant with a permucosal or percutaneous component. In some embodiments, the implant may be a prosthetic limb element.

In other embodiments, the adhesive compositions might be injected, layered, sprayed, brushed, or otherwise applied in one or more variants of composition to a surgical wound in areas where the bony tissue is present near the gingiva, mucosa, skin, or other element of the integument, thereby fixating the soft tissue margins and blocking movement of liquids, materials, and microbiota and their products deeper into the wound.

In other embodiments, the adhesive compositions may be used to reconstruct and adjoin a fissure or gap that has resulted from a congenital deformity, such as, but not limited to a cleft lip and palate. The compositions could be utilized to restore the bone deformity to a primary palate by using the compositions to fill and adhere the maxillary and medial nasal processes.

In other embodiments, the adhesive compositions may be used in the field of plastic surgery as an onlay graft, which can be applied and adheres to the outer surfaces of bone in the facial region. The composition may be adhesively applied as a fluid or putty like substance, and contoured or molded to a desired cosmetic profile or contour before it hardens. The composition may be resorbed and replaced by bone over time, while maintaining the original volume and shape formed during application. The composition could be applied, but not limited, to the chin, cheek, mid-face, or forehead regions.

In some embodiments, the adhesive compositions may be adhesively applied to affix the bone fragment removed to create a window to allow access for grafting in a sinus lift procedure or a Caldwell-Luc procedure. The adhesive composition may be injected, sprayed, brushed or otherwise applied in one or more compositional variants to fill the gap and/or affix the bony fragment or flap created by surgical instruments to allow access to the sinus cavity.

In some embodiments, the compositions may be adhesively applied to affix the bone fragment or fragments removed to create access for procedures within spaces enclosed by bone (e.g., intracranial space for brain surgery procedures). In some embodiments, creating access within spaces enclosed by bone comprises providing cranial flap access to the incranial space, e.g., for brain surgery procedures. The adhesive composition may be injected, sprayed, brushed or otherwise applied, in one or more compositional variants, to affix the bony fragment, bone fragments, or bone flap to the anatomical site from which it was removed in the course of gaining the said access by surgical instruments.

In some embodiments, the adhesive compositions may be applied to obdurate an opening in bone or a communication between spaces or potential spaces separated by the said bone. This opening might be a congenitally, pathologically, traumatically or surgically generated bony fenestration, dehiscence, or communication (e.g., oral-antral fistula, Caldwell-Luc procedure access opening, sinus elevation graft access opening) or any other. The adhesive composition may be injected, sprayed, brushed or otherwise applied in one or more compositional variants, in conjunction or without other materials possibly serving as carrier or matrix, to occlude the passage from one to another side of the bone through gap, fistula, or communication channel.

In some embodiments, the adhesive composition might serve as a seal to close off the communication between an intracranial or spinal space bathed in the cerebrospinal fluid and the exterior of the body: the method comprising: a) preparation of an adhesive composition comprising a multivalent metal salt and a small organic phosphate compound in an aqueous solution or suspension; b) application of the adhesive composition into or onto said communication, e.g., crevice, fistula, or tear; and c) allowing the composition to remain undisturbed until the composition is hardened, cured, or resorbed and replaced by bone.

In some embodiments, the disclosure features a method of adhesively repairing a defect in a tooth, the method comprising: a) preparation of an adhesive composition comprising a multivalent metal salt and a small organic phosphate compound in an aqueous solution or suspension; b) application of the composition into or onto said tooth defect; and c) allowing the composition to remain undisturbed until the composition is hardened, cured, or resorbed and replaced by bone.

In some embodiments, the adhesive compositions may be adhesively applied to the surface of a tooth. The adhesive composition may be injected, sprayed, brushed or otherwise applied in one or more compositional variants to fill the gap in tooth substance resulting from the removal of dental caries or to a surface exposed by tooth fracture or abrasion, attrition, or erosion of the tooth substance.

In some embodiments, the adhesive compositions may be adhesively applied to the surface of a tooth or dental restorative material to lute or adhesively fixate them. The adhesive composition may be injected, sprayed, brushed or otherwise applied in one or more compositional variants to fill the gap in tooth substance resulting from the removal of dental caries or to a surface exposed by tooth fracture or abrasion, attrition, or erosion of the tooth substance.

In some embodiments, different variants of the components of the adhesive composition may be packaged and marketed as a kit for specific indications.

In some embodiments, said kits may comprise a container containing a multivalent metal salt (e.g., calcium phosphates or calcium oxide) with a compound of Formula (I) (e.g., a small organic phosphate compound, e.g., phosphoserine) present together and sealed under good packaging practices to preserve the shelf life of the individual components. In some embodiments, preservation of the shelf life of the components within the kit includes maintenance of sterility. If additives are included in said kit, they may be packaged within this container or within a separate container. The aqueous medium (e.g., solution or suspension), if included, may be provided in a separate container. The kit may include additional components for the preparation or application of the adhesive compositions, such as mixing bowls or surfaces, stirring sticks, spatulas, syringes, heat guns, or other preparation or delivery devices.

In some embodiments, the adhesive compositions may adopt a pliable working state after mixing with an aqueous solution or suspension prior to hardening, which is present for up to about 30 minutes or less, depending on the components of said compositions. In some embodiments, the adhesive compositions may adopt a pliable working state for less than or equal to about 30 minutes after mixing with an aqueous solution or suspension, e.g., less than about 20 minutes, less than about 15 minutes, less than about 10 minutes, less than about 5 minutes, less than about 3 minutes, less than about 2 minutes, less than about 1 minute, less than about 30 seconds, less than about 5 seconds after mixing with an aqueous solution or suspension.

In some embodiments, after a set amount of time, the adhesive compositions may adopt a hard, cement-like state. This process of conversion from the pliable working state to the cement-like state may be referred to as "hardening," "curing," or "setting." In some embodiments, the adhesive compositions may exhibit an adhesive strength in the cement-like state in the range of about 100 kPa to about 12,000 kPa, depending on the application and the particular components and ratios of components in said adhesive compositions. In some embodiments, the adhesive strength of the adhesive compositions in the cement-like state is between about 100 kPa and e.g., about 10,000 kPa, about 9,000 kPa, about 8,000 kPa, about 7,000 kPa, about 6,000 kPa, about 5,000 kPa, about 4,000 kPa, about 3,000 kPa, about 2,000 kPa, about 1,000 kPa, about 750 kPa, about 500 kPa, about 250 kPa, or about 200 kPa. In some embodiments, the adhesive strength of the adhesive compositions in the cement-like state is between about 100 kPa, about 200 kPa, about 300 kPa, about 400 kPa, about 500 kPa, about 600 kPa, about 700 kPa, about 800 kPa, about 900 kPa, about 1,000 kPa, about 2,500 kPa, about 5,000 kPa, about 7,500 kPa, about 10,000 kPa or about 12,000 kPa. In some embodiments, the adhesive strength of the adhesive compositions in the cement-like state is in the range of about 200 kPa and about 2,500 kPa. In some embodiments, the particular components of the adhesive compositions may be selected to achieve the desired strength depending on the intended use of the adhesive compositions. In all embodiments, a skilled practitioner (e.g., a doctor, dentist, surgeon, nurse, or other suitable person) may alter the specific components to achieve the desired adhesive properties of said composition based on the intended use or desired outcome.

In other embodiments, the adhesive compositions are used to treat or heal a subject suffering from a disease or condition, such as cancer (e.g., osteosarcoma), osteoporosis, rickets, osteogenesis imperfecta, fibrous dysplasia, Paget's disease of the bone, hearing loss, renal osteodystrophy, a malignancy of the bone, infection of the bone, severe and handicapping malocclusion, osteonecrosis, or other genetic or developmental disease. In some embodiments, the adhesive compositions are used to repair a defect in a bone caused by a disease or condition, such as cancer (e.g., osteosarcoma), osteoporosis, rickets, osteogenesis imperfecta, fibrous dysplasia, Paget's disease of the bone, hearing loss, renal osteodystrophy, a malignancy of the bone, infection of the bone, or other genetic or developmental disease. In some embodiments, the adhesive compositions are used to strengthen a bone in a subject that has been weakened by a disease or condition, such as cancer (e.g., osteosarcoma), osteoporosis, rickets, osteogenesis imperfecta, fibrous dysplasia, Paget's disease of the bone, hearing loss, renal osteodystrophy, a malignancy of the bone, infection of the bone, or other genetic or developmental disease. In some embodiments, the subject has experienced a trauma, such as a broken bone, fractured bone, or damaged tooth. In some embodiments, the subject has experienced tooth decay. In some embodiments, the subject is undergoing a plastic surgery procedure. The compositions and methods may be used to treat a subject suffering from or afflicted with any disease or condition that impacts the structural integrity of the bony skeleton. In some embodiments, the subject is a child. In some embodiments, the subject is an adult. In some embodiments, the subject is a non-human animal.

In some embodiments, the adhesive composition comprises at least one of tetracalcium phosphate, phosphoserine, hydroxyapatite, alpha tricalcium phosphate, beta tricalcium phosphate, calcium oxide, sorbitol, poly(lactide-co-glycolide), or water. In some embodiments, the adhesive composition comprises at least two of tetracalcium phosphate, phosphoserine, hydroxyapatite, alpha tricalcium phosphate, beta tricalcium phosphate, calcium oxide, sorbitol, poly(lactide-co-glycolide), or water. In some embodiments, the adhesive composition comprises at least three of tetracalcium phosphate, phosphoserine, hydroxyapatite, alpha tricalcium phosphate, beta tricalcium phosphate, calcium oxide, sorbitol, poly(lactide-co-glycolide), or water.

In some embodiments, the adhesive composition comprises tetracalcium phosphate, phosphoserine, and water (e.g., as exemplified by Composition A in Table 1). In some embodiments, the adhesive composition comprises tetracalcium phosphate, phosphoserine, alpha tricalcium phosphate, and water (e.g., as exemplified by Composition B in Table 1). In some embodiments, the adhesive composition comprises tetracalcium phosphate, phosphoserine, beta tricalcium phosphate, and water (e.g., as exemplified by Composition C in Table 1). In some embodiments, the adhesive composition comprises phosphoserine, alpha tricalcium phosphate, calcium oxide, and water (e.g., as exemplified by Composition D in Table 1). In some embodiments, the adhesive composition comprises tetracalcium phosphate, phosphoserine, sorbitol, and water (e.g., as exemplified by Composition E in Table 1). In some embodiments, the adhesive composition comprises tetracalcium phosphate, phosphoserine, hydroxyapatite, and water (e.g., as exemplified by Composition F in Table 1). In some embodiments, the adhesive composition comprises tetracalcium phosphate, phosphoserine, hydroxyapatite, poly(lactide-co-glycolide), and water (e.g., as exemplified by Composition G in Table 1).

In some embodiments, the adhesive composition has an adhesive strength (e.g., an average shear stress strength) greater than 0.5 MPa (e.g., greater than about 0.75 MPa, about 1.0 MPa, about 1.25 MPa, about 1.5 MPa, about 2 MPa, about 2.5 MPa, or about 3.0 MPa). In some embodiments, the adhesive composition comprises tetracalcium phosphate, phosphoserine, and water (e.g., as exemplified by Composition A in Table 1) and has an adhesive strength (e.g., an average shear stress strength) greater than 1 MPa (e.g., greater than 1.25 MPa, about 1.5 MPa, about 2 MPa, about 2.5 MPa, or about 3.0 MPa). In some embodiments, the adhesive composition comprises tetracalcium phosphate, phosphoserine, alpha tricalcium phosphate, and water (e.g., as exemplified by Composition B in Table 1) and has an adhesive strength (e.g., an average shear stress strength) greater than 1 MPa (e.g., greater than 1.25 MPa, about 1.5 MPa, about 2.0 MPa, about 2.5 MPa, or about 3.0 MPa). In some embodiments, the adhesive composition comprises tetracalcium phosphate, phosphoserine, beta tricalcium phosphate, and water (e.g., as exemplified by Composition C in Table 1) and has an adhesive strength (e.g., an average shear stress strength) greater than 1 MPa (e.g., greater than 1.25 MPa, about 1.5 MPa, about 2 MPa, about 2.5 MPa, or about 3.0 MPa). In some embodiments, the adhesive composition comprises phosphoserine, alpha tricalcium phosphate, calcium oxide, and water (e.g., as exemplified by Composition D in Table 1) and has an adhesive strength (e.g., an average shear stress strength) greater than 1 MPa (e.g., greater than 1.25 MPa, about 1.5 MPa, about 2 MPa, about 2.5 MPa, or about 3.0 MPa). In some embodiments, the adhesive composition comprises tetracalcium phosphate, phosphoserine, sorbitol, and water (e.g., as exemplified by Composition E in Table 1) and has an adhesive strength (e.g., an average shear stress strength) greater than 1 MPa (e.g., greater than 1.25 MPa, about 1.5 MPa, about 2 MPa, about 2.5 MPa, or about 3.0 MPa). In some embodiments, the adhesive composition comprises tetracalcium phosphate, phosphoserine, hydroxyapatite, and water (e.g., as exemplified by Composition F in Table 1) and has an adhesive strength (e.g., an average shear stress strength) greater than 1 MPa (e.g., greater than 1.25 MPa, about 1.5 MPa, about 2 MPa, about 2.5 MPa, or about 3.0 MPa). In some embodiments, the adhesive composition comprises tetracalcium phosphate, phosphoserine, hydroxyapatite, poly(lactide-co-glycolide), and water (e.g., as exemplified by Composition G in Table 1) and has an adhesive strength (e.g., an average shear stress strength) greater than 1 MPa (e.g., greater than 1.25 MPa, about 1.5 MPa, about 2 MPa, about 2.5 MPa, or about 3.0 MPa).

EXAMPLES

Some embodiments presented herein are further described in detail by reference to the following examples. These examples are provided for purposes of illustration and are not intended to be limiting unless otherwise specified. The disclosure should be construed to encompass any and all variations which become evident as a result of the teaching provided herein.

Without further description, it is believed that one of ordinary skill in the art can, using the preceding description and the following illustrative examples, make and utilize the compounds and practice the claimed methods. The following examples specifically point out various aspects of the disclosure, and are not to be construed as limiting in any way the remainder of the disclosure.

Example 1

Exemplary adhesive compositions are outlined in Table 1. The solid components listed in the table were combined in a suitable receptacle and mixed with water to achieve the desired consistency. While water was used in the compositions summarized in the table, the aqueous medium in the present composition may instead be blood, saliva, serum, or a blood-based solution. The solid components listed in the table may be supplied in particle, granule, or fiber form, and the size of each of the components listed in Table 1 may range as described in the Detailed Description. In some embodiments, the resulting properties such as working and setting time would be affected by these changes. The specific mean particle, granule, or fiber size for each solid component was be selected to satisfy the use requirements as described in each of the embodiments.

The quantities of each of the components listed may be altered or adjusted in relation to the other components in the composition. After mixing, the compositions described were applied to the desired site and the adhesive properties examined, e.g., for tensile strength and durability. Each composition may further comprise phases and ingredients not indicated in the table.

TABLE 1

Components of Exemplary Adhesive Compositions

| Component | Composition | | | | | | |
|---|---|---|---|---|---|---|---|
| | A | B | C | D | E | F | G |
| Tetracalcium phosphate | 800 mg | 800 mg | 800 mg | 0 | 800 mg | 800 mg | 800 mg |
| Phosphoserine | 500 mg | 500 mg | 500 mg | 500 mg | 500 mg | 500 mg | 500 mg |
| Hydroxyapatite | 0 | 0 | 0 | 0 | 0 | 375 mg | 375 mg |

TABLE 1-continued

Components of Exemplary Adhesive Compositions

| Component | Composition | | | | | | |
|---|---|---|---|---|---|---|---|
| | A | B | C | D | E | F | G |
| Alpha Tricalcium Phosphate | 0 | 375 mg | 0 | 675 mg | 0 | 0 | 0 |
| Beta Tricalcium Phosphate | 0 | 0 | 375 mg | 0 | 0 | 0 | 0 |
| Calcium oxide | 0 | 0 | 0 | 125 mg | 0 | 0 | 0 |
| Sorbitol | 0 | 0 | 0 | 0 | 100 mg | 0 | 0 |
| Poly(lactide-co-glycolide) | 0 | 0 | 0 | 0 | 0 | 0 | 50 mg |
| Water | 270 μL | 270 μL | 320 μL | 270 μL | 240 μL | 320 μL | 340 μL |

Example 2

In this example, the compositions described in Table 1 were tested for bone-bone or bone-titanium adhesive shear strength. The bone cubes used for shear testing were prepared from a bovine femur cortical source, and the metal cubes used for shear testing were Highly Corrosion-Resistant Grade 2 Titanium with an alumina blasted finish. Each cube used for testing was rectangular with dimensions of 8.5 mm×8.5 mm×20 mm. The surfaces adhered were the 8.5 mm×8.5 mm faces from two cubes. The bone cubes were stored at −20° C. prior to testing to preserve their structure. Prior to testing, the bone cubes were removed from the freezer and pre-conditioned by submerging them in a phosphate buffered saline (PBS) bath at 37° C. for at least one hour. Immediately prior to testing, the bone cubes were removed from the bath and excess aqueous solution was not removed from the surface (i.e., the surfaces were wet). The titanium cubes were also pre-conditioned by submerging them in a phosphate buffered saline (PBS) bath at 37° C. for at least one hour prior to testing.

Each composition in Table 1 was mixed for t=20 seconds in a 25 mL capacity silicone mixing bowl using a stainless steel spatula. After mixing, the composition was loaded into a 3 cc capacity slip tip syringe. The composition was immediately injected onto one end of each of the 8.5 mm×8.5 mm surfaces of two cubes by t=1.5 minutes after the start of mixing. Immediately thereafter, the cube surfaces covered with adhesive composition were apposed and excess material that squeezed out which surrounded the perimeter of the external surfaces of the joint was removed with a spatula. The adjoined cubes were placed into a fixture that applied a slight compressive force (3-5 N) for 4 minutes from the start of mixing corresponding to the working period of the compositions from the start of mixing. Thereafter, the cubes were removed from the fixture and submerged into a PBS bath at 37° C. to allow the compositions to cure until the indicated time. The adhered set of cubes were tested at either t=10 minutes, t=1 hour, or t=24 hours from the start of mixing. After the cure time indicated, the cubes were removed from the PBS bath for shear testing. The proximal cube of the adhered cube set was secured in a stable fashion to prevent movement within a sample holding fixture up to within 1.0 mm of the adhered joint within an Instron® 5969 axial load frame. The distal cube of the adhered cube set was cantilevered from the sample holding fixture. When the bone-titanium cube set was tested, the titanium cube was the distal cube. The Instron crosshead with an attached anvil fixture was lowered until the distal surface of the anvil was within 0.5 mm of the top surface of the distal bone cube and within 1.0 mm of adhered joint. The test was run with the crosshead speed at 2 mm/minute.

Table 2 shows the results for the bone-bone average shear stress (MPa) and standard deviation along with the number of replicates for each test group. Table 3 shows the results for the bone-titanium average shear stress (MPa) and standard deviation along with the number of replicates for each test group. NT means that particular test group was not tested. The results show the compositions had adhesive strength, wherein the average shear stress for both the adhered bone-bone and bone-titanium cubes for each of the compositions tested exceeded 1 MPa.

TABLE 2

Bone-Bone Adhesive Shear Testing of the Adhesive Compositions

| | Bone-Bone | | | | | | | | |
|---|---|---|---|---|---|---|---|---|---|
| | 10 Minutes | | | 1 Hour | | | 24 Hour | | |
| Composition | Average (MPa) | St.Dev. (MPa) | n | Average (MPa) | St.Dev. (MPa) | n | Average (MPa) | St.Dev. (MPa) | n |
| A | 2.08 | 0.69 | 6 | 2.49 | 0.37 | 6 | 3.57 | 0.99 | 6 |
| B | NT | NT | 0 | 2.89 | 1.21 | 4 | NT | NT | 0 |
| C | 1.60 | 0.21 | 6 | 2.50 | 0.44 | 5 | 3.03 | 0.57 | 6 |
| D | NT | NT | 0 | 2.06 | 0.46 | 3 | NT | NT | 0 |
| E | NT | NT | 0 | 1.86 | 1.61 | 4 | NT | NT | 0 |
| F | 3.02 | 1.00 | 8 | 2.63 | 0.71 | 8 | 3.11 | 0.86 | 7 |
| G | 2.21 | 0.65 | 4 | 1.68 | 0.96 | 3 | 3.67 | 1.44 | 5 |

TABLE 3

Bone-Titanium Adhesive Shear Testing of the Adhesive Compositions
Bone-Titanium

| 10 Minutes | | | 1 Hour | | | 24 Hour | | |
|---|---|---|---|---|---|---|---|---|
| Average (MPa) | St.Dev. (MPa) | n | Average (MPa) | St.Dev. (MPa) | n | Average (MPa) | St.Dev. (MPa) | n |
| NT | NT | 0 | 2.34 | 0.32 | 6 | NT | NT | 0 |
| NT | NT | 0 | NT | NT | 0 | NT | NT | 0 |
| 1.45 | 0.24 | 2 | 1.84 | 0.30 | 2 | 2.52 | 0.13 | 2 |
| NT | NT | 0 | NT | NT | 0 | NT | NT | 0 |
| NT | NT | 0 | NT | NT | 0 | NT | NT | 0 |
| NT | NT | 0 | NT | NT | 0 | NT | NT | 0 |
| NT | NT | 0 | NT | NT | 0 | NT | NT | 0 |

Example 3

In this example, a composition described in Table 1 may be used in any embodiment described herein, but in particular could be used to fill an extraction socket of the alveolar bone, fill a periodontal defect of the alveolar bone, fill a cystic defect of the alveolar bone, perform a sinus lift, and or to augment the ridge of the alveolar bone, before, during, or after placement of a dental implant. Likewise, the compositions could be used to fixate adjacent vertebrae in a spinal fusion surgery with or without the use of instrumentation. The composition may be used with or without internal metal fixation, and may be mixed with autograft or allograft as a bone graft extender.

Example 4

In this example, an adhesive composition described in Table 1 is used to fill a void or gap in a bone due to the removal of a bone cyst, granuloma, or similar bone defect crestal or lateral to the alveolar ridge. After preparing the composition, the material is applied to said void or gap and allowed to become solid. Upon solidification, the tensile strength and durability of the material will be tested.

Example 5

In this example, an adhesive composition described in Table 1 is used to repair a defect in a bone in a subject suffering from a disorder such as cancer (e.g., osteosarcoma), osteoporosis, rickets, osteogenesis imperfecta, fibrous dysplasia, Paget's disease of the bone, hearing loss, renal osteodystrophy, a malignancy of the bone, infection of the bone, osteonecrosis, or other genetic or developmental disease. After preparing the composition, the material is applied to said void or gap and allowed to become solid. The solidification process may be hastened through the use of a heat gun or other heating element.

The subject may be an adult that requires one or more applications of the adhesive composition in order to fully repair the bone defect. Further, the site of application may be weakened by the disorder, such that additives may be used in the adhesive composition to enhance the functional properties of the composition. Exemplary additives include medications, antimicrobial agents, flavoring agents, and the like.

Example 6: Bone Void Filler (Jaw Bone)—Alveolar Ridge Preservation in Maxilla—Bone Regeneration at t=3 Weeks (Canine)

Composition A as outlined in Table 1 was implanted into the alveolus of a fresh extraction socket as a ridge preservation graft in the maxilla of a canine. A dental membrane was not utilized for repair to prevent microbial ingress, to prevent migration of the composition, or to prevent fibrous tissue ingress and suturing was not employed to close the wound, i.e., the healing proceeded by secondary intention over Composition A. FIGS. 23A and 23B illustrate the graft at t=3 weeks post-operatively (decalcified sections, Hematoxylin and Eosin (H&E)). As shown, viable osteocytes and osteoblasts abound and new bone surrounds Composition A (TA). FIG. 23A shows the graft site, the tooth root (R), the presence of new woven bone (NWB), the absence of excessive acute inflammatory cells or soft tissue ingrowth. FIG. 23B is a higher magnification image of the framed zone. Note the presence of osteocytes in the lacunae (black arrows) in pre-existing alveolar bone (AB); the presence of osteoblasts (blue arrows) and osteoid is direct evidence of new bone apposition. As shown, the adhesive composition (Composition A) did not migrate from the graft site and served as a barrier to prevent ingress of microbes that could cause an infection and prevented fibrous tissue ingress into the graft site.

Example 7: Bone Void Filler (Jaw Bone)—Alveolar Ridge Preservation in Mandible—Bone Regeneration at t=21 Weeks (Canine)

Figures 24A, 24B, 24C:
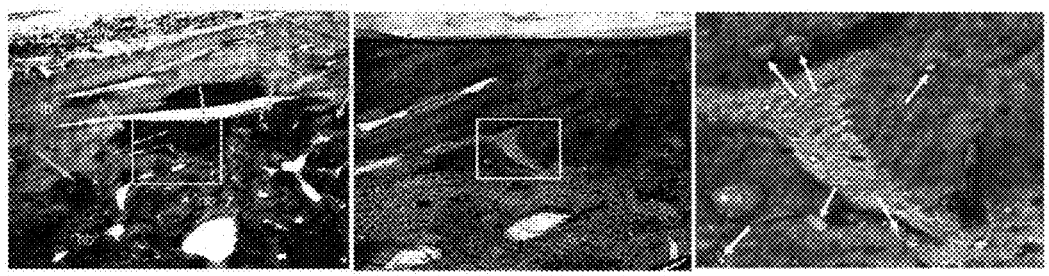
Figures 25A, 25B, 25C, 25D, 25E, 25F:
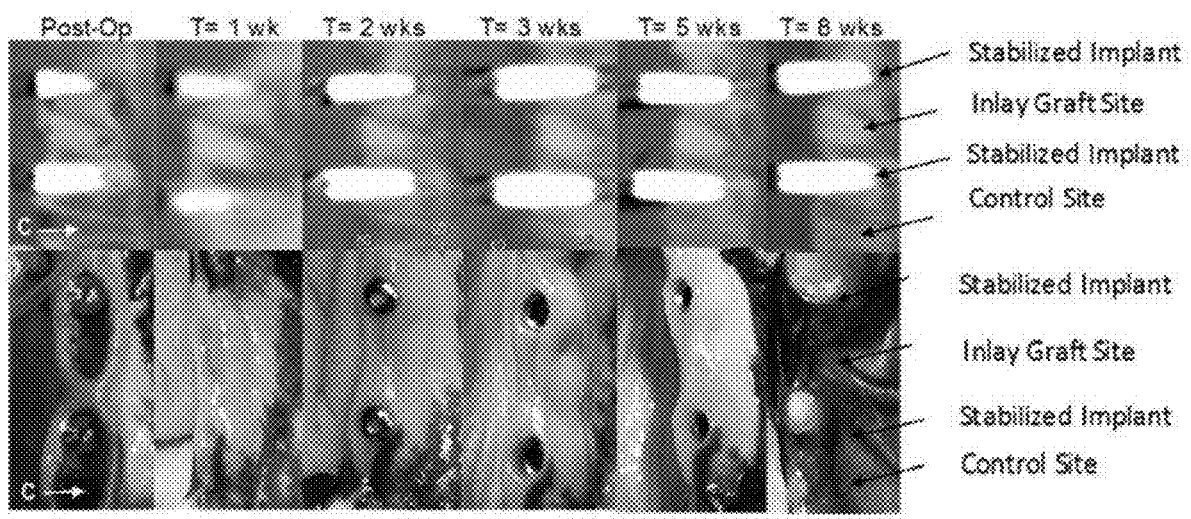
FIG. 25 shows a series of images depicting the response to exemplary adhesive Composition F, from directly after the operation (FIG. 25A), to 1 week (FIG. 25B), 2 weeks (FIG. 25C), 3 weeks (FIG. 25D), 5 weeks (FIG. 25E) and 8 weeks (FIG. 25F) post-operation.

Composition C as outlined in Table 1 was implanted into the alveolus of a fresh extraction socket as a ridge preservation graft in the mandible of a canine. A dental membrane was not utilized for repair to prevent microbial ingress, to prevent migration of the composition, or to prevent fibrous tissue ingress and suturing was not employed to close the wound, i.e., the healing proceeded by secondary intention over Composition C. FIGS. 24A-24C illustrate the graft at t=21 weeks post-operatively (ground section, H&E). The low power image (FIG. 24A) of the inlay deposit of Composition C shows old cortical lamellar bone (lb), mucosa (mu) and newly laid down bone (nb). FIG. 24B shows the framed detail at higher magnification. The new bone is a mixture of woven and lamellar bone at this point, revealing a low bone deposition rate. The highest magnification image (FIG. 24C) shows the detail of the framed section of FIG. 24B. Note the presence of residual granular material from Composition C present within the bone tissue (white arrows) which indicates that this composition is capable of regenerating bone as the bulk of the material resorbs at t=21 weeks. As shown, the adhesive composition did not migrate from the graft site and served as a barrier to prevent ingress of microbes that could cause an infection and prevented fibrous tissue ingress into the graft site.

Example 8: Bone Void Filler and Implant Stabilization (Jaw Bone)—Alveolar Ridge Preservation and Implant Fixation in Mandible—Bone Regeneration Through t=8 Weeks (Canine)

Composition F as outlined in Table 1 was implanted into fresh extraction sockets of the premolar teeth, P2 and P3, in the mandible of a canine. Composition F was adhesively implanted as an inlay graft for ridge preservation in the distal alveolus of the premolar P3 site, whereas Composition F was adhesively applied to provide primary fixation of a dental implant following osteotomies of the mesial alveolus for the P2 and P3 sites to create oversized defects relative to the dental implant artificially creating a model to demonstrate the use of the adhesive composition for stabilizing a dental implant. A healing screw was installed onto the dental implant after the composition hardened. A dental membrane was not utilized for repair to prevent microbial ingress, to prevent migration of the composition, or to prevent fibrous tissue ingress and suturing was not employed to close the wound, i.e., the healing proceeded by secondary intention over Composition F.

The healing of the implantation sites was assessed through t=8 weeks post operatively using Cone Beam Computed Tomography (CBCT) and clinical examination as depicted in FIGS. 25A-25F. The top row of images illustrates the CBCT appearance of a) site of ridge preservation depositing Composition F as an inlay graft in the P3 site and b) sites of stabilized implants depositing Composition F to adhere the dental implants into oversized osteotomies of the P2 and P3 sites. The bottom row of images shows the clinical appearance of the sites at the same time points. Note the healthy appearance of tissues surrounding the deposited composition with consistently low level of inflammation present at removal of the healing screw. The adhesive composition did not migrate from the graft site and served as a barrier to prevent ingress of microbes that could cause an infection and prevented fibrous tissue ingress into the graft site. Note an unfilled extraction socket served as a (c) control site.

Figure 26:
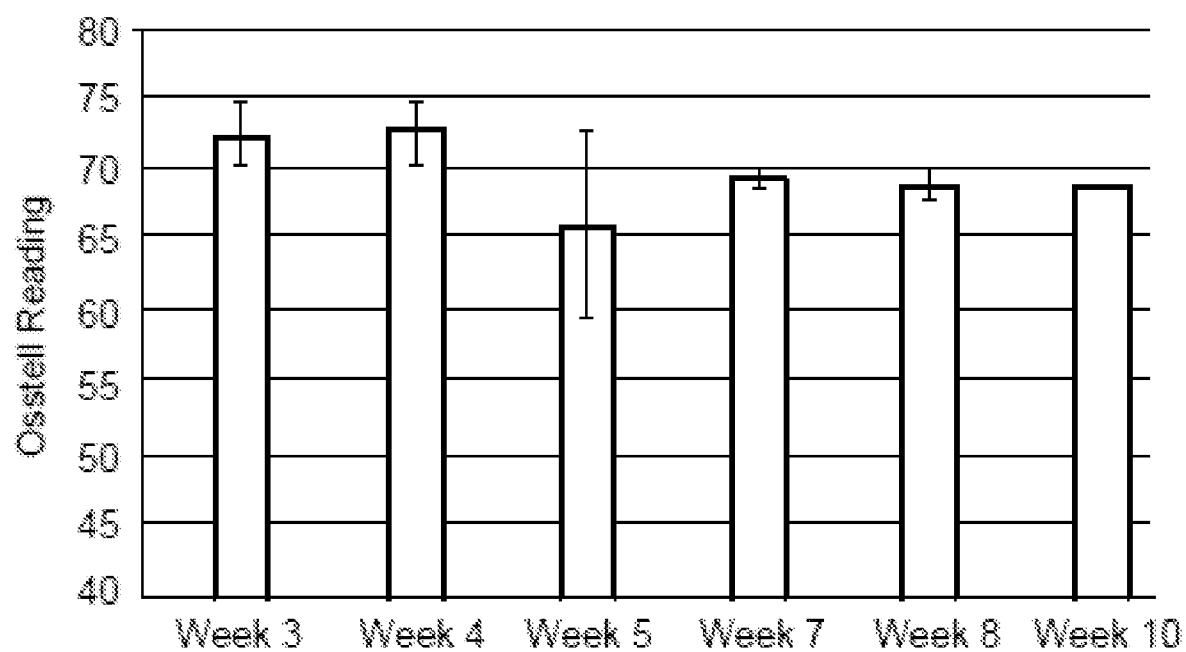
FIG. 26 is a chart showing the implant stability (Ostell reading) of mandibular implants provided by exemplary adhesive Composition F from 3 weeks post-operative through 10 weeks.

The stability of dental implants adhered in oversized P3 and P4 osteotomy sites using Composition F was assessed using an Osstell meter at weekly evaluations through t=10 weeks. The average reading from the buccal, mesial, and lingual sides are taken for each of the dental implants as displayed in FIG. 26. The stability of dental implants adhered with Composition F shows that the implant is stable since the average ISQ value is above 65 at every time point assessed, wherein ISQ values above 50 is clinically meaningful to indicate implant is stable enough to allow for loading.

Example 9: Implant Stabilization (Jaw Bone)—Alveolar Ridge Implant Fixation in Mandible—Bone Regeneration at t=9 Weeks (Canine)

Composition C as outlined in Table 1 was adhesively applied to provide primary fixation of a dental implant following tooth extraction and an osteotomy of the mesial alveolus for the mandibular P2 site of a canine to create oversized defects relative to the dental implant artificially creating a model to demonstrate the use of the adhesive composition for stabilizing an implant. A transmucosal abutment and a crown were installed onto the dental implant during the same surgical visit once Composition C hardened. A dental membrane was not utilized for repair to prevent microbial ingress, to prevent migration of the composition, or to prevent fibrous tissue ingress and suturing was not employed to close the wound, i.e., the healing proceeded by secondary intention over Composition F. The subject dog transitioned from soft food diet to a hard foot diet t=45 days after surgery which imparted load through the dental implant and adhesive composition. A histological examination of the dental implant and Composition C used to adhere the implant into an oversized osteotomy site in a canine mandible t=9 weeks post-operatively (ground sections, H&E) yields photomicrographic images shown in FIGS. 27A-27B. Two views of the field are presented: bright field (FIG. 27A) and UV fluorescence (FIG. 27B); tetracycline IV, was given t=3 days prior to sacrifice. The images show extensive new bone apposition (nb) onto the Composition C surface (TN) and nascent bone spicules (B). Newest bone laid down fluoresces as bright in the right image. Note the adjacent tooth root (R), lacking fluorochrome uptake, and the monocytic phagocytes removing TN material. Also note the dental implant (IM) underlying the TN more clearly visible in the UV fluorescence image. As shown, the adhesive composition did not migrate from the graft site and served as a barrier to prevent ingress of microbes that could cause an infection and prevented fibrous tissue ingress into the graft site. This study demonstrates that an adhesive composition (e.g., an adhesive composition described herein) can be applied to stabilize a dental implant that is fully restored into an alveolar site deficient in bone volume and which is subjected to loading following surgery.

Example 10: Onlay Graft (Jaw Bone)—Alveolar Ridge Augmentation—Bone Volume Expansion and Maintenance Through t=10 Weeks (Canine)

Composition F as outlined in Table 1 was adhesively applied as an onlay deposit by injection subperiosteal to the outer buccal surface of alveolar bone near the maxillary cuspid tooth in a hound dog for ridge augmentation to increase bone volume. Dental membranes or fixation were not utilized for repair and stabilization of the composition. The animals were monitored by Cone Beam Computed Tomography (CBCT) and clinical exam weekly. Findings of radiographic examinations through t=10 weeks post-operatively are shown in FIGS. 28A-28G. The images show the coronal plane CBCT images. This study demonstrates the ability of an adhesive composition (e.g., an adhesive composition described herein) to adhere to the cortical surface of the jaws without being mobile evaluated through manual palpation during the weekly clinical exams while maintaining augmented volume and being replaced by bone without the use of dental membranes or fixation. The adhesive composition served as a barrier to prevent ingress of microbes that could cause an infection and prevented fibrous tissue ingress into the graft site. Note the remodeling of the graft mass attended by its decalcification.

Example 11: Onlay Graft (Jaw Bone)—Alveolar Ridge Augmentation—Bone Volume Expansion at t=9 Weeks (Canine)

Composition C as outlined in Table 1 was adhesively applied as an onlay deposit by injection subperiosteally to the outer buccal surface of alveolar bone near the maxillary cuspid tooth in a beagle dog for ridge augmentation to increase bone volume. Dental membranes or fixation were not utilized for repair and stabilization of the composition. The animals were monitored by CBCT and clinical exam weekly. Findings of clinical and radiographic examinations at t=9 weeks post-operatively are shown in FIGS. 29A-29C. FIG. 29A is a clinical photograph of the site of interest. FIG. 29B shows a superimposed pre-operative and t=9 weeks post-operatively 3D CT reconstruction, filtered at bone density, of the adhesion composition deposit and the surroundings. FIG. 29C is a cone beam CT (CBCT) image of a parapalatal plane section through the grafted area of Composition C (TN). Note the volume of the graft deposit continuous with buccal bone overlying the cuspid root cross-section (C). This study demonstrates the ability of an adhesive composition (e.g., an adhesive composition described herein) to adhere to the cortical surface of the jaws without being mobile evaluated through manual palpation during the clinical exams while maintaining augmented volume and being replaced by bone without the use of dental membranes or fixation. The adhesive composition served as a barrier to prevent ingress of microbes that could cause an infection and prevented fibrous tissue ingress into the graft site.

Example 12: Adhesive Bone Bridging—Posterolateral Fusion of Lumbar Vertebrae without Instrumentation at t=3 Weeks (Rabbit)

Composition G was used to perform both spinal fixation without instrumentation under a load bearing model utilizing New Zealand White Rabbits similar to the Boden study (Boden, S. D. et al. Spine (1995) 20:412-420). Composition G was injected bilaterally at the L5/L6 vertebral levels between the transverse processes then along the pars interarticularis and allowed to cure, thus forming a solid bridge. These vertebral levels bridged by Composition G were isolated and extracted for ex vivo testing as shown in FIG. 30 after t=3 weeks (n=1), t=6 weeks (n=2), and t=10 weeks (n=2) postoperatively to assess the fixation tensile strength.

Figure 31:
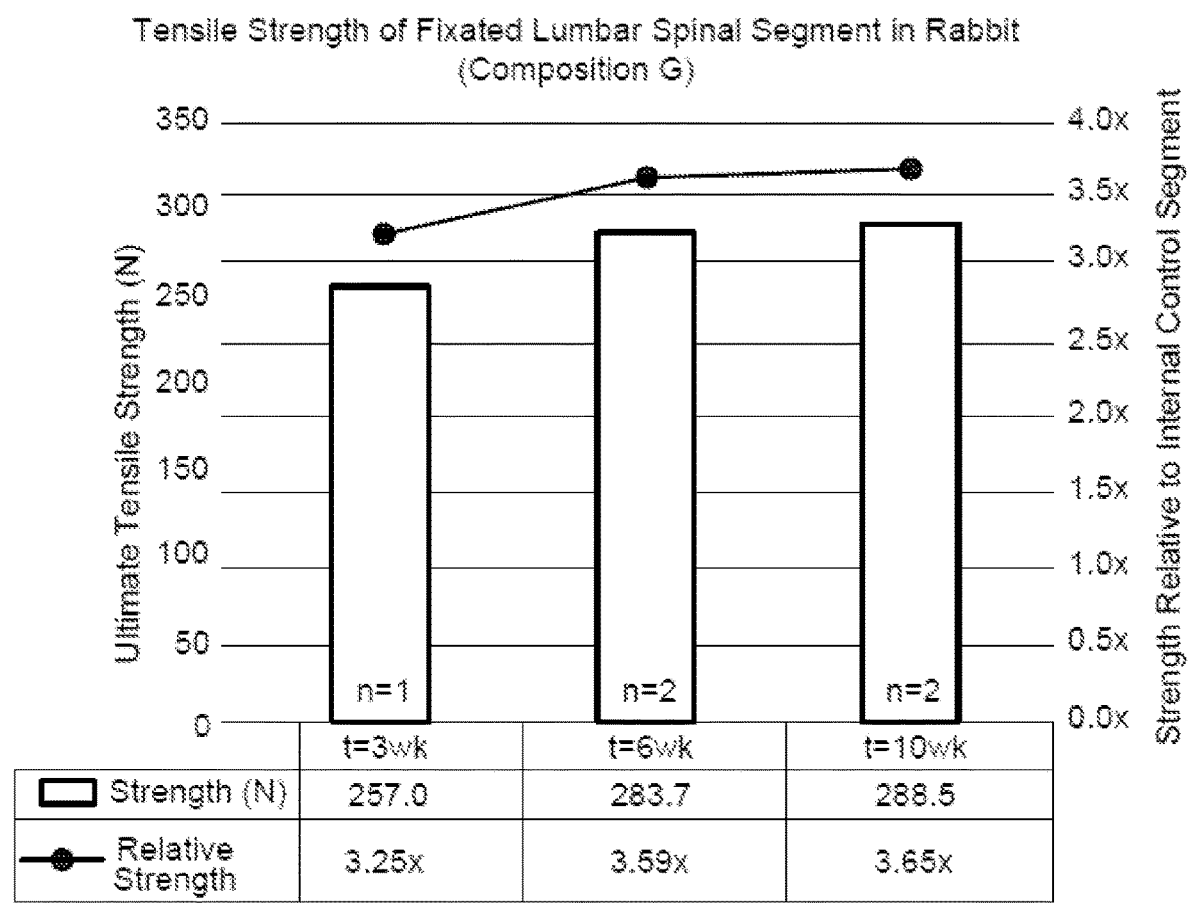
FIG. 31 is a graph showing mechanical tensile test results from obtained from adjacent rabbit spinal vertebral bodies (L5/L6) fixated with exemplary adhesive Composition G to bridge the gap between transverse processes (bilateral) as shown in FIG. 30 through 10 weeks.

The adjacent, non-fused level (L4/L5) was tested to create an internal control. A plot of these results is shown in FIG. 31. At t=3 weeks, t=6 weeks, and t=10 weeks the vertebrae treated with Composition G showed a marked increase in relative load bearing strength when compared to the control of 3.25×, 3.59×, and 3.65× respectively, which demonstrates the load bearing capacity of the adhesive composition to maintain spinal fixation without the use of instrumentation.

Figures 32A, 32B, 32C:
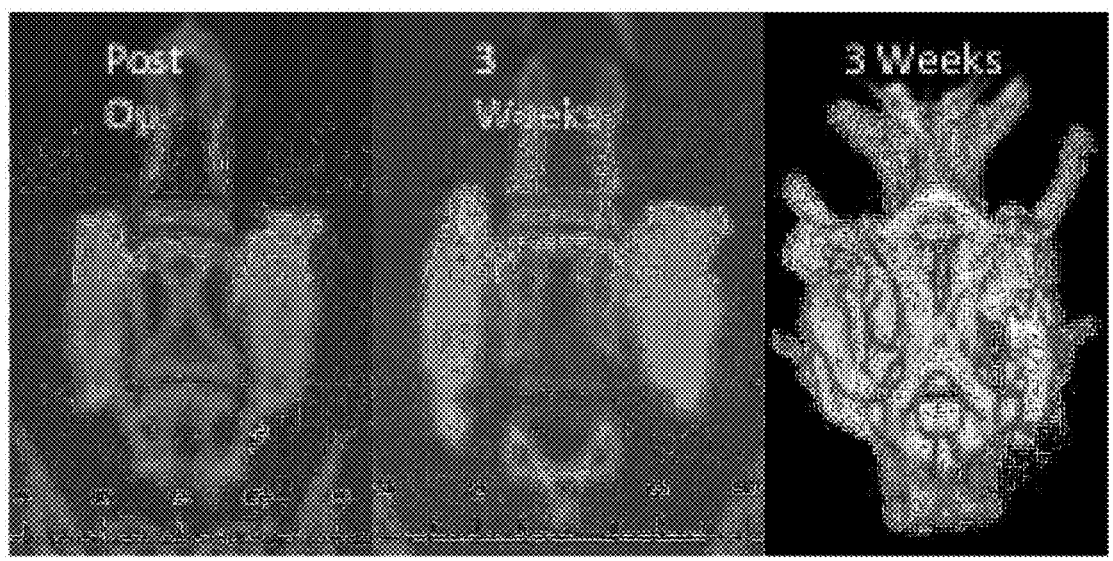

Additionally, CBCT scans were completed post-operatively and on a weekly schedule until sacrifice of each of the rabbits in the study. An example set of the CBCT images taken from the rabbit sacrificed at t=3 weeks is shown in FIGS. 32A-32C. FIG. 32A shows the spine post operatively, FIG. 32B shows the spine at t=3 weeks postoperatively, and FIG. 32C shows a 3D rendering of the spine at t=3 weeks postoperatively. The CBCT images show that the adhesive composition did not migrate from the graft site, that spinal fixation was achieved and that stability was maintained without fracture over time.

EQUIVALENTS

The disclosures of each and every patent, patent application, and publication cited herein are hereby incorporated herein by reference in their entirety. While this disclosure has been described with reference to specific aspects, it is apparent that other aspects and variations may be devised by others skilled in the art without departing from the true spirit and scope of the disclosure. The appended claims are intended to be construed to include all such aspects and equivalent variations. Any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference.

While this disclosure has been particularly shown and described with references to preferred embodiments thereof, it will be understood by those skilled in the art that various changes in form and details may be made therein without departing from the scope of the disclosure encompassed by the appended claims.

We claim:

1. A method of joining two or more bones, bone fragments, or bone segments with an injectable adhesive composition, the method comprising injecting the adhesive composition in a fluid state onto or into the bones, bone fragments, or bone segments to be joined;
wherein the adhesive composition comprises an organic phosphate compound, a multivalent metal salt selected from tetracalcium phosphate or tricalcium phosphate, and an aqueous medium, the injectable adhesive composition comprising about 10% to about 35% aqueous medium to provide for a viscosity between 100 cP and 10,000 cP when in the fluid state;
the multivalent metal salt is provided as a powder; and
the mean particle size of the powder particles is between 0.005 mm and 0.150 mm;
thereby joining two or more bones, bone fragments, or bone segments.

2. The method of claim 1, further comprising preparing the bone, bone fragment, or bone segment prior to injecting the adhesive composition.

3. The method of claim 2, wherein the preparing comprises milling, drilling, or reaming.

4. The method of claim 1, wherein the adhesive composition hardens over time into a cement-like state in about 30 minutes.

5. The method of claim 1, further comprising applying a compressive force to the bones, bone fragments, or bone segments to be joined prior to, during, and/or after injecting the adhesive composition.

6. The method of claim 4, wherein the adhesive composition exhibits an adhesive strength in the cement-like state of between 100 kPa and 12,000 kPa.

7. The method of claim 1, wherein multivalent metal salt is present within the adhesive composition in an amount between 30% and 75% (w/w) of the total weight.

8. The method of claim 1, wherein the multivalent metal salt is tricalcium phosphate.

9. The method of claim 8, wherein the tricalcium phosphate comprises α-tricalcium phosphate or β-tricalcium phosphate.

10. The method of claim 1, wherein the multivalent metal salt is tetracalcium phosphate.

11. The method of claim 1, wherein the organic phosphate compound is a compound of Formula (I) or a salt thereof:

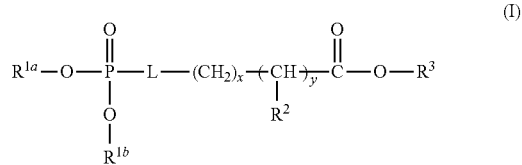

wherein:
L is O, S, NH, or $CH_2$;
each of $R^{1a}$ and $R^{1b}$ is independently H, optionally substituted alkyl, or optionally substituted aryl;
$R^2$ is H, $NR^{4a}R^{4b}$, $C(O)R^5$, or $C(O)OR^5$;
$R^3$ is H, optionally substituted alkyl, or optionally substituted aryl;
each of $R^{4a}$ and $R^{4b}$ is independently H, $C(O)R^6$, or optionally substituted alkyl;
$R^5$ is H, optionally substituted alkyl, or optionally substituted aryl;
$R^6$ is optionally substituted alkyl or optionally substituted aryl; and
each of x and y is independently 0, 1, 2, or 3.

12. The method of claim 1, wherein the organic phosphate compound comprises phosphoserine.

13. The method of claim 1, wherein the organic phosphate compound is present within the adhesive composition in an amount between 10% and 90% (w/w) of the total weight.

14. The method of claim 1, wherein the aqueous medium comprises water, saliva, saline, serum, plasma, or blood.

15. The method of claim 1, wherein the adhesive composition further comprises an additive.

16. The method of claim 15, wherein the additive comprises a salt, filler, formulation base, viscosity modifier, abrasive, coloring agent, flavoring agent, or polymer.

17. The method of claim 16, wherein the polymer comprises poly(L-lactide), poly(D,L-lactide), polyglycolide, poly(ε-caprolactone), poly(teramethylglycolic-acid), poly(dioxanone), poly(hydroxybutyrate), poly(hydroxyvalerate), poly(lactide-co-glycolide), poly(glycolide-co-trimethylene carbonate), poly(glycolide-co-caprolactone), poly(glycolide-co-dioxanone-co-trimethylene-carbonate), poly(tetramethylglycolic-acid-co-dioxanone-co-trimethylenecarbonate), poly(glycolide-co-caprolactone-co-lactide-co-trimethylene-carbonate), poly(hydroxybutyrate-co-hydroxyvalerate), poly(methylmethacrylate), poly(acrylate), polyamines, polyamides, polyimidazoles, poly(vinyl-pyrrolidone), collagen, silk, chitosan, hyaluronic acid, gelatin, or a mixture thereof.

18. The method of claim 1, wherein the mean particle size of the powder particles is between 0.060 mm and 0.150 mm.

\* \* \* \* \*